United States Patent
Zhang et al.

(10) Patent No.: US 8,710,092 B2
(45) Date of Patent: Apr. 29, 2014

(54) SUBSTITUTED INDOLO 4,3 FG QUINOLINES USEFUL FOR TREATING MIGRAINE

(75) Inventors: Jian Zhang, Sunnyvale, CA (US); Robert O. Cook, Hillsborough, NJ (US); Thomas A. Armer, Cupertino, CA (US); Sergey Alexandrovich Kosarev, Singapore (SG); Dejian Xie, Shanghai (CN)

(73) Assignee: Map Pharmaceuticals, Inc., Irvine, CA (US)

( * ) Notice: Subject to any disclaimer, the term of this patent is extended or adjusted under 35 U.S.C. 154(b) by 0 days.

(21) Appl. No.: 12/978,314

(22) Filed: Dec. 23, 2010

(65) Prior Publication Data

US 2011/0152280 A1 Jun. 23, 2011

Related U.S. Application Data

(60) Provisional application No. 61/289,987, filed on Dec. 23, 2009.

(51) Int. Cl.
*A61K 31/40* (2006.01)

(52) U.S. Cl.
USPC .......................... 514/410; 548/218; 548/428

(58) Field of Classification Search
USPC .................................. 514/410; 548/218, 425
See application file for complete search history.

(56) References Cited

U.S. PATENT DOCUMENTS

| | | | |
|---|---|---|---|
| 2,886,568 | A | 5/1959 | Stansbury, Jr. et al. |
| 3,113,133 | A | 12/1963 | Hofmann et al. |
| 3,190,884 | A | 6/1965 | Hofmann et al. |
| 3,218,324 | A | 11/1965 | Hofmann et al. |
| 3,336,311 | A | 8/1967 | Hofmann et al. |
| 3,536,809 | A | 10/1970 | Applezweig |
| 3,586,683 | A | 6/1971 | Sadler et al. |
| 3,598,123 | A | 8/1971 | Zaffaroni |
| 3,652,569 | A | 3/1972 | Stadler et al. |
| 3,666,762 | A | 5/1972 | Guttmann et al. |
| 3,681,355 | A | 8/1972 | Guttmann et al. |
| 3,710,795 | A | 1/1973 | Higuchi et al. |
| 3,755,328 | A | 8/1973 | Sadler et al. |
| 3,814,765 | A | 6/1974 | Bernardi et al. |
| 3,845,770 | A | 11/1974 | Theeuwes et al. |
| 3,916,899 | A | 11/1975 | Theeuwes et al. |
| 3,922,347 | A | 11/1975 | Bach et al. |

(Continued)

FOREIGN PATENT DOCUMENTS

| | | | |
|---|---|---|---|
| CH | 610330 | * | 1/1979 |
| EP | 0296748 | | 4/1993 |

(Continued)

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Fluckiger, et al. Developments in Endocrinology (Amsterdam), 2, 1978, 383-396.*
Aellig, W.H., et al., Effect of Natural and Synthetic Polypeptide Type Ergot Compounds on a Peripheral Vascular Bed, *Brit. J. Pharmacol.*, 1969, 36(3): 561-570.

(Continued)

*Primary Examiner* — Douglas M Willis
(74) *Attorney, Agent, or Firm* — Jennifer C. Cheng; Sunil K. Singh; Syndicated Law, P.C.

(57) ABSTRACT

Provided herein are substituted indolo[4,3-fg]quinolines of Formula (I) and (II) where $R_1$-$R_6$ and $R_{13}$ are as defined in the specification and pharmaceutical compositions thereof which are useful in treating, preventing, or ameliorating a variety of medical disorders such as, for example, migraine.

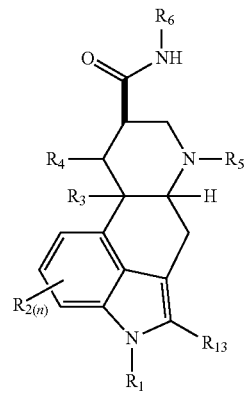

(I)

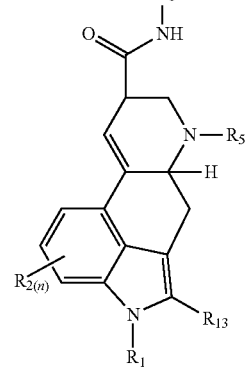

(II)

In other embodiments, provided herein are methods of agonizing receptors such as, for example, the 5-$HT_{1D}$ and or 5-$HT_{1B}$ receptor using the compounds and compositions disclosed herein. In still other embodiments, provided herein are methods of antagonizing or inhibiting activity at receptors such as, for example, the 5-$HT_{2B}$ receptor using the compounds and compositions disclosed herein. In still other embodiments, provided herein are methods of regulating serotonin transport using the compounds and compositions disclosed herein.

19 Claims, 5 Drawing Sheets

(56) References Cited

U.S. PATENT DOCUMENTS

| | | | |
|---|---|---|---|
| RE28,819 E | 5/1976 | Thompson | |
| 4,005,089 A | 1/1977 | Mago et al. | |
| 4,008,719 A | 2/1977 | Theeuwes et al. | |
| 4,044,126 A | 8/1977 | Cook et al. | |
| 4,124,712 A * | 11/1978 | Stutz et al. | 514/249 |
| 4,165,376 A | 8/1979 | Rosenberg | |
| 4,230,854 A | 10/1980 | Beacco et al. | |
| 4,328,245 A | 5/1982 | Yu et al. | |
| 4,358,603 A | 11/1982 | Yu | |
| 4,364,923 A | 12/1982 | Cook et al. | |
| 4,409,239 A | 10/1983 | Yu | |
| 4,410,545 A | 10/1983 | Yu | |
| 4,414,209 A | 11/1983 | Cook et al. | |
| 4,522,811 A | 6/1985 | Eppstein et al. | |
| 4,675,404 A | 6/1987 | Bernardi et al. | |
| 4,804,660 A | 2/1989 | Kobel et al. | |
| 5,033,252 A | 7/1991 | Carter | |
| 5,052,558 A | 10/1991 | Carter | |
| 5,059,595 A | 10/1991 | Le Grazie | |
| 5,073,543 A | 12/1991 | Marshall, I et al. | |
| 5,120,548 A | 6/1992 | Mcclelland et al. | |
| 5,158,957 A | 10/1992 | Brumby et al. | |
| 5,323,907 A | 6/1994 | Kalvelage | |
| 5,354,556 A | 10/1994 | Sparks et al. | |
| 5,401,748 A | 3/1995 | Sauer et al. | |
| 5,591,767 A | 1/1997 | Mohr et al. | |
| 5,639,476 A | 6/1997 | Oshlack et al. | |
| 5,639,480 A | 6/1997 | Bodmer et al. | |
| 5,668,155 A | 9/1997 | Cincotta et al. | |
| 5,674,533 A | 10/1997 | Santus et al. | |
| 5,705,510 A | 1/1998 | DeSantis et al. | |
| 5,709,874 A | 1/1998 | Hanson et al. | |
| 5,733,566 A | 3/1998 | Lewis | |
| 5,739,108 A | 4/1998 | Mitchell | |
| 5,759,542 A | 6/1998 | Gurewich | |
| 5,840,674 A | 11/1998 | Yatvin et al. | |
| 5,860,957 A | 1/1999 | Jacobsen et al. | |
| 5,877,183 A | 3/1999 | Cincotta et al. | |
| 5,891,474 A | 4/1999 | Busetti et al. | |
| 5,900,252 A | 5/1999 | Calanchi et al. | |
| 5,922,356 A | 7/1999 | Koseki et al. | |
| 5,948,433 A | 9/1999 | Burton et al. | |
| 5,972,366 A | 10/1999 | Haynes et al. | |
| 5,972,891 A | 10/1999 | Kamei et al. | |
| 5,980,945 A | 11/1999 | Ruiz | |
| 5,983,134 A | 11/1999 | Ostrow | |
| 5,985,307 A | 11/1999 | Hanson et al. | |
| 5,985,317 A | 11/1999 | Venkateshwaran et al. | |
| 5,993,855 A | 11/1999 | Yoshimoto et al. | |
| 6,004,534 A | 12/1999 | Langer et al. | |
| 6,010,715 A | 1/2000 | Wick et al. | |
| 6,024,975 A | 2/2000 | D'angelo et al. | |
| 6,039,975 A | 3/2000 | Shah et al. | |
| 6,045,830 A | 4/2000 | Igari et al. | |
| 6,048,736 A | 4/2000 | Kosak | |
| 6,060,082 A | 5/2000 | Chen et al. | |
| 6,071,495 A | 6/2000 | Unger et al. | |
| 6,087,324 A | 7/2000 | Igari et al. | |
| 6,113,943 A | 9/2000 | Okada et al. | |
| 6,120,751 A | 9/2000 | Unger | |
| 6,131,570 A | 10/2000 | Schuster et al. | |
| 6,139,865 A | 10/2000 | Friend et al. | |
| 6,167,301 A | 12/2000 | Flower et al. | |
| 6,197,350 B1 | 3/2001 | Yamagata et al. | |
| 6,221,870 B1 | 4/2001 | Pfaeffli et al. | |
| 6,248,363 B1 | 6/2001 | Patel et al. | |
| 6,253,872 B1 | 7/2001 | Neumann | |
| 6,256,533 B1 | 7/2001 | Yuzhakov et al. | |
| 6,261,595 B1 | 7/2001 | Stanley et al. | |
| 6,264,970 B1 | 7/2001 | Hata et al. | |
| 6,267,981 B1 | 7/2001 | Okamoto et al. | |
| 6,267,983 B1 | 7/2001 | Fujii et al. | |
| 6,271,359 B1 | 8/2001 | Norris et al. | |
| 6,274,552 B1 | 8/2001 | Tamarkin et al. | |
| 6,316,652 B1 | 11/2001 | Steliou | |
| 6,376,461 B1 | 4/2002 | Igari et al. | |
| 6,419,961 B1 | 7/2002 | Igari et al. | |
| 6,589,548 B1 | 7/2003 | Oh et al. | |
| 6,613,358 B2 | 9/2003 | Randolph et al. | |
| 6,699,500 B2 | 3/2004 | Okada et al. | |
| 6,740,634 B1 | 5/2004 | Saikawa et al. | |
| 6,855,707 B2 | 2/2005 | Cincotta et al. | |
| 7,217,822 B2 | 5/2007 | Comin et al. | |
| 7,666,877 B2 | 2/2010 | Baenteli et al. | |
| 8,178,529 B2 | 5/2012 | Arvidsson et al. | |
| 2007/0020299 A1 | 1/2007 | Pipkin et al. | |
| 2007/0225312 A1 | 9/2007 | Ludwig et al. | |
| 2009/0264456 A1 | 10/2009 | Sewell et al. | |
| 2010/0048587 A1 | 2/2010 | Cook et al. | |
| 2010/0081663 A1 | 4/2010 | Cook et al. | |
| 2010/0226943 A1 | 9/2010 | Brennan et al. | |
| 2011/0152280 A1 | 6/2011 | Cook et al. | |
| 2012/0329806 A1 | 12/2012 | Cook et al. | |

FOREIGN PATENT DOCUMENTS

| | | |
|---|---|---|
| GB | 1485738 | 9/1977 |
| WO | WO-97/46239 A1 | 12/1997 |
| WO | WO02-49608 A1 | 6/2002 |
| WO | WO2005-025506 A2 | 3/2005 |
| WO | WO2005-025506 A3 | 3/2006 |
| WO | WO2012-177962 | 6/2012 |

OTHER PUBLICATIONS

Beran, M., et al., Ergot Alkaloids. LXXIII. 9,10-Dihydroergopeptines Modified in Position 6, *Collect. Czech. Chem. Commun*, 1990, 55(3): 819-832.

Buchwald, H., et al., Long-Term, continuous Intravenous Heparin Administration by an Implantable Infusion Pump in Ambulatory Patients with Recurrent Venous Thrombosis, *Surgery*, 1980, 88(4): 507-516.

International Search Report and Written Opinion for PCT/US2010/62098, Mar. 20, 2011, MAP Pharmaceuticals, Inc.

Goernemann, T., et al., Pharmacological Properties of a Wide Array of Ergolines at Functional Alpha1-Adrenoceptor Subtypes, *Naunyn-Schmiedeberg's Arch. Pharmacol.*, 2008, 376(5): 321-330.

Goodson, J.M., Dental Applications, *Medical Applications of Controlled Release*, vol. II, Chapter 6, pp. 115-138, CRC Press, Inc., Boca Raton, FL, 1984.

Langer, R., New Methods of Drug Delivery, *Science*, 1990, 249(4976): 1527-1533.

Guillory, K., Chapter 5, pp. 202-205, 205-208 in Polymorphism in Pharmaceutical Solids, (Brittain, H. ed.), Marcel Dekker, Inc. New York, 1999.

Brittain, H., Chapter 6, pp. 227-278 in Polymorphism in Pharmaceutical Solids, (Brittain, H. ed.), Marcel Dekker, Inc. New York, 1999.

Saudek, C.D., et al., A Preliminary Trial of the Programmable Implantable Medication System for Insulin Delivery, *N. Eng.. J. Med.*, 1989, 321: 574-579.

Schreier, E., Ergot Alkaloids. 83. Radiolabeled Peptide Ergot Alkaloids, *Helvetica Chimica Acta*, 1976, 59(2): 585-606.

Sefton, M.V., Implantable Pumps, *Crit. Rev. Biomed. Eng.*, 1987, 14(3): 201-240.

Weber, H.P., The Molecular Architecture of Ergopeptines: a Basis for Biological Interaction, *Adv. Biochem. Psychopharmacol.*, 1980, 23, 25-34.

Buchwald, H. et al., Long-Term, continuous intravenous Heparin Administration by an Implantable Infusion Pump in Ambulatory Patients with Recurrent Venous Thrombosis, Surgery, 1980, 88(4): 507-516.

Carstensen, Jens T., Drug Stability: Principles & Practice, 2d. Ed., Marcel Dekker, NY, NY, 1995, pp. 379-380.

Castro, Enhancement of Oral Absorption in Selective 5-HT1D Receptor Agonists: Fluorinated 3-[3-(Piperidin-1-yl)propyl]indoles, J. Med. Chem. 41: 2667-2670 (1998).

Egan, et al. Agonist Activity of LSD and lisuride at cloned 5HT2A and 5HTC receptors, Psychopharmacology (1998) 136:409-414.

Ennis, Isochroman-6-carboxamides as Highly Selective 5-HT1D Agonists: Potential New Treatment for Migraine without Cardiovascular Side Effects, J. Med. Chem.41:2180-2183 (1998).

(56) References Cited

OTHER PUBLICATIONS

International Search Report and Written Opinion mailed Aug. 28, 2012, for PCT/US2012/043687.
International Search Report and Written Opinion mailed Sep. 12, 2012, for PCT/US2012/043686.
International Search Report and Written Opinion mailed Sep. 19, 2012, for PCT/US2012/043681.
Kalani, et al. The Predicted 3D structure of the human D2 dopamine receptor and the binding site and binding affinities for agaonists and antagonists. PNAS, 2004, vol. 101(11), pp. 3815-3820, p. 3816, col. 2, para 2-p. 3819, col. 2, para 3. Downloaded at www.pnas.org/content/101/11/3815.long.
Newman-Tancredi, Differential Actions of Antiparkinson Agents at Multiple Classes of Monoaminergic Receptor.II. Agonist and Antagonist Properties at Subtypes of Dopamine D2-Like Receptor and a1/a2-Adrenoceptor, J Pharmacology and Experimental Therapies 303(2):805-814, 2002.
Phebus, Cephalalgia 17: 245 (1997). Abstract Only.
Rothman, Evidence for Possible Involvement of 5-HT2B Receptors in the Cardiac Valvulopathy Associated with Fenfluramine and other Serotonergic Medications, Circulation 102: 2836-2841 (2000).
Schaerlinger, Agonist actions of dihydroergotamine at 5-HT2B and 5-HT2C receptors and their possible relevance to antimigraine efficacy, Br. J.Pharmacol. 140(2): 277-84, (2003).
Slassi, 5-Alkyltryptamine Derivatives as Highly Selective and Potent 5-HT1D Receptor Agonists, Bioorg. Med. Chem. Lett. 10: 1707-1709 (2000).
International Search Report and Written Opinion mailed Sep. 12, 2012, for PCT/US2012/043677.
Silberstein, et al. Ergotamine and Dihydroergotamine: History, Pharmacology, and Efficacy, Headache 43(2): 144-166 (2003).
Cook, et al. Reduced Adverse Event Profile of Orally Inhaled DHE (MAP0004) vs IV DHE: Potential Mechanism, Headache 49(10): 1423-1434 (2009).
Hofmann, et al. Fast estimation of crystal densities, Acta Crystallographica B57: 489-493 (2002).
Marini, et al. Physico-Chemical Characterization of Drugs and Drug Forms in the Solid State, Curr. Med. Chem 2(4): 303-321 (2003).
McClurg, et al. X-ray Powder Diffraction Pattern Indexing for Pharmaceutical Applications, Pharm. Tech. Europe, http://www.pharmtech.com/pharmtech/Peer-Reviewed+Research/X-ray-Powder-Diffraction-Pattern-Indexing-for-Phar/ArticleStandard/Article/detail/800851, 7 pgs. (Jan. 2013).
Notice of Allowance dated Aug. 22, 2013, for U.S. Appl. No. 13/531,371, filed Jun. 22, 2012.
Notice of Allowance dated Sep. 5, 2013, for U.S. Appl. No. 13/531,416, filed Jun. 22, 2012.

\* cited by examiner

SUBSTITUTED INDOLO 4,3 FG QUINOLINES USEFUL FOR TREATING MIGRAINE

This application claims priority under 35 U.S.C. §119 (e) from U.S. Provisional Application Ser. No. 61/289,987, filed Dec. 23, 2009, which is hereby incorporated by reference in its entirety.

FIELD

Provided herein are novel ergoline derivatives and pharmaceutical compositions thereof. In other embodiments, provided herein are methods of treatment, prevention, or amelioration of a variety of medical disorders such as, for example, migraine using the compounds and compositions disclosed herein. In still other embodiments, provided herein are methods of agonizing receptors such as, for example, the $5\text{-HT}_{1B}$ and or $5\text{-HT}_{1D}$ receptor using the compounds and compositions disclosed herein. In still other embodiments, provided herein are methods of antagonizing or inhibiting activity at receptors such as, for example, the $5\text{-HT}_{2B}$ receptor using the compounds and compositions disclosed herein. In still other embodiments, provided herein are methods of regulating serotonin transport using the compounds and compositions disclosed herein.

BACKGROUND

Many naturally occurring and synthetic ergolines are known to bind in a non-specific manner to receptors for the bioamine neurotransmitters, e.g., dopamine, noradrenaline and serotonin and to function as agonists or antagonists for these compounds at these receptors. Developing compounds that are selective or specific for certain specific receptors allows for achievement of desirable therapeutic actions while eliminating or reducing unwanted side effects and accordingly is an important challenge. For example, selective serotonin antagonists have been developed for the treatment of migraine and more recently, selective dopamine agonists for the treatment of Parkinson's disease and hyperprolactinemia have been discovered.

However, there is a continuing need for less toxic and more selective ergoline derivatives to treat a variety of disorders such as, for example, migraines wherein selective agonism (e.g., $5\text{-HT}_{1D}$ and $5\text{-HT}_{1B}$) and antagonism (e.g., $5\text{-HT}_{2B}$) neurotransmitters receptors are preferable.

SUMMARY

Provided herein are ergoline derivatives which address these and other needs. In one aspect, the ergoline derivatives described herein include compounds of structural Formula (I):

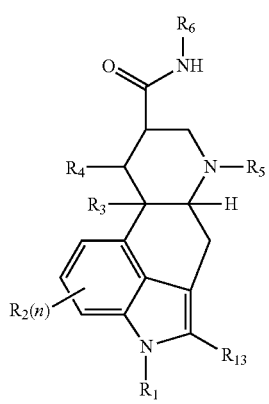

(I)

or salts, hydrates or solvates thereof wherein:

$R_1$ is $(C_1\text{-}C_4)$ alkyl, substituted $(C_1\text{-}C_4)$ alkyl or $(C_1\text{-}C_4)$ perfluoroalkyl;

$R_2$ is alkyl, substituted alkyl, acyl, substituted acyl, halo, heteroalkyl, substituted heteroalkyl, —$NO_2$, —$N_3$, —OH, —$S(O)_k R_{100}$, —$OR_{101}$, —$NR_{102}R_{103}$, —$CONR_{104}R_{105}$, —$CO_2R_{106}$ or —$O_2CR_{107}$;

$R_3$ and $R_4$ are independently hydrogen, deuterium, fluoro, hydroxy or methoxy;

$R_5$ is hydrogen, $(C_1\text{-}C_3)$ alkyl, substituted $(C_1\text{-}C_4)$ alkyl or $(C_1\text{-}C_3)$ perfluoroalkyl;

$R_6$ is

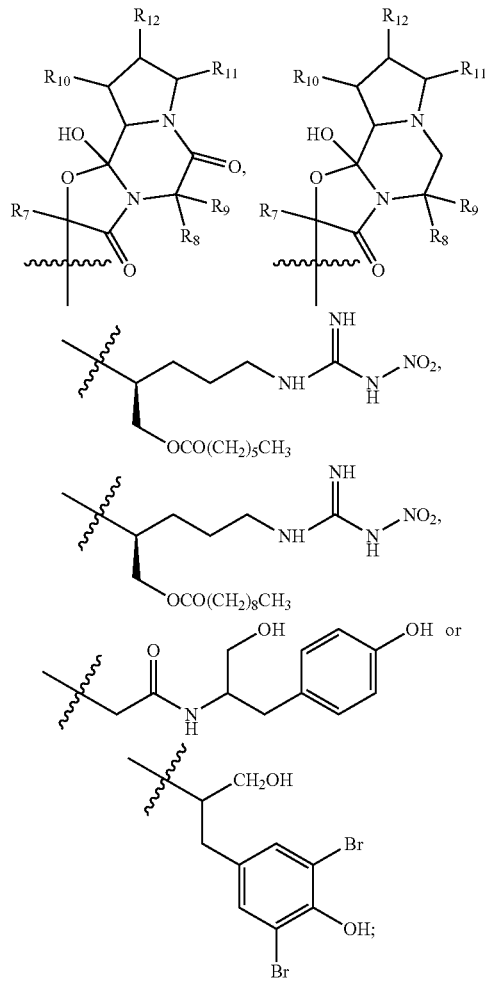

$R_7$ is $(C_1\text{-}C_4)$ alkyl;

$R_8$ is hydrogen, $(C_1\text{-}C_4)$ alkyl, substituted $(C_1\text{-}C_4)$ alkyl, benzyl or substituted benzyl;

$R_9$ is $(C_1\text{-}C_4)$ alkyl or benzyl;

$R_{10}$ is hydrogen, OH, =O, $(C_1\text{-}C_4)$ alkyl, $(C_1\text{-}C_4)$ substituted alkyl, —$CO_2R_{108}$ or —$CONR_{109}R_{110}$;

$R_{11}$ is hydrogen, OH, =O, $(C_1\text{-}C_4)$ alkyl, $(C_1\text{-}C_4)$ substituted alkyl, —$CO_2R_{111}$ or —$CONR_{112}R_{113}$;

$R_{12}$ is hydrogen, OH, =O, $(C_1\text{-}C_4)$ alkyl, $(C_1\text{-}C_4)$ substituted alkyl, —$CO_2R_{414}$ or —$CONR_{115}R_{116}$;

$R_{13}$ is hydrogen or halogen;

$R_{101}$-$R_{116}$ are independently hydrogen, alkyl, substituted alkyl, acyl, substituted acyl, aryl, substituted aryl, arylalkyl, substituted arylalkyl, heteroalkyl, substituted hetereoalkyl, heteroaryl, substituted heteroaryl, heteroarylalkyl or substituted heteroarylalkyl; and k is 0, 1 or 2;
n is 0, 1, 2 or 3;
provided that when $R_1$ and $R_5$ are methyl, $R_2$, $R_3$, $R_4$, $R_{10}$, $R_{11}$, $R_{12}$ and $R_{13}$ are hydrogen and $R_6$ is

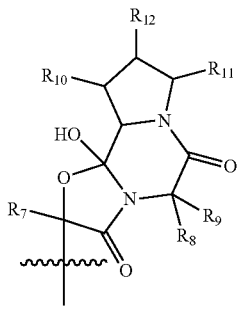

that:
$R_7$ is not methyl, $R_8$ is not hydrogen and $R_9$ is not sec-butyl;
$R_7$ is not methyl, $R_8$ is not hydrogen and $R_9$ is not benzyl;
$R_7$ is not n-butyl, $R_8$ is not methyl and $R_9$ is not methyl;
$R_7$ is not isopropyl, $R_8$ is not methyl and $R_9$ is not benzyl;
$R_7$ is not isopropyl, $R_8$ is not hydrogen and $R_9$ is not n-propyl;
$R_7$ is not isopropyl, $R_8$ is not hydrogen and $R_9$ is not isobutyl;
$R_7$ is not isopropyl, $R_8$ is not hydrogen and $R_9$ is not isopropyl;
$R_7$ is not ethyl, $R_8$ is not hydrogen and $R_9$ is not isobutyl;
provided that when $R_1$ and $R_5$ are methyl, $R_3$ is —OH, $R_2$, $R_4$, $R_{10}$, $R_{11}$, $R_{12}$ and $R_{13}$ are hydrogen and $R_6$ is

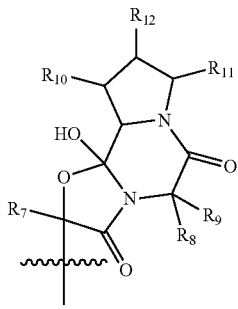

that:
$R_7$ is not methyl, $R_8$ is not hydrogen and $R_9$ is not sec-butyl;
provided that when $R_1$ and $R_5$ are methyl, $R_3$ is —OCH$_3$, $R_2$, $R_4$, $R_{10}$, $R_{11}$, $R_{12}$ and $R_{13}$ are hydrogen and $R_6$ is

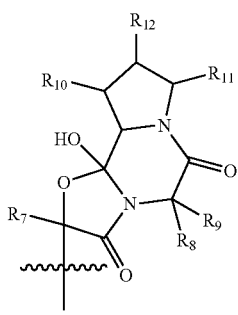

that:
$R_7$ is not methyl, $R_8$ is not hydrogen and $R_9$ is not sec-butyl;
$R_7$ is not isopropyl, $R_8$ is not hydrogen and $R_9$ is not isopropyl;
$R_7$ is not isopropyl, $R_8$ is not hydrogen and $R_9$ is not benzyl;
$R_7$ is not methyl, $R_8$ is not hydrogen and $R_9$ is not benzyl;
$R_7$ is not methyl, $R_8$ is not hydrogen and $R_9$ is not sec-butyl;
provided that when $R_1$ and $R_5$ are methyl, $R_2$, $R_3$, $R_4$, $R_{10}$, $R_{11}$ and $R_{12}$ are hydrogen, $R_{13}$ is bromine and $R_6$ is

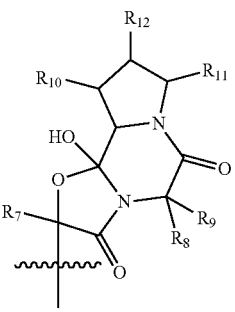

that:
$R_7$ is not methyl, $R_8$ is not hydrogen and $R_9$ is not benzyl;
$R_7$ is not methyl, $R_8$ is not hydrogen and $R_9$ is not isopropyl;
$R_7$ is not isopropyl, $R_8$ is not hydrogen and $R_9$ is not isopropyl;
$R_7$ is not isopropyl, $R_8$ is not hydrogen and $R_9$ is not isobutyl;
provided that when $R_1$ is n-propyl, $R_5$ is methyl, $R_2$, $R_3$, $R_4$, $R_{10}$, $R_{11}$ and
$R_{12}$ are hydrogen, $R_{13}$ is bromine and $R_6$ is

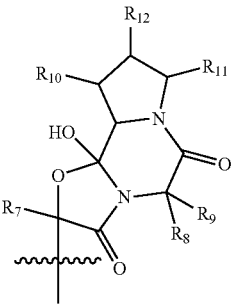

that:
$R_7$ is not isopropyl, $R_8$ is not hydrogen and $R_9$ is not isopropyl;
provided that when $R_1$ and $R_5$ are methyl, $R_2$, $R_3$, $R_4$, $R_{10}$, $R_{11}$ and $R_{12}$ are
hydrogen, $R_{13}$ is iodine and $R_6$ is

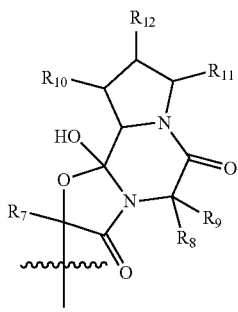

that:

R$_7$ is not methyl, R$_8$ is not hydrogen and R$_9$ is not benzyl;

provided that when R$_1$ is methyl, R$_5$ is n-propyl, R$_2$, R$_3$, R$_4$, R$_{10}$, R$_{11}$, R$_{12}$ and R$_{13}$ are hydrogen and R$_6$ is

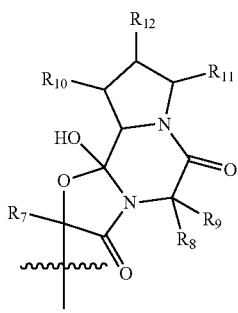

that:

R$_7$ is not isopropyl, R$_8$ is not hydrogen and R$_9$ is not benzyl;

R$_7$ is not methyl, R$_8$ is not hydrogen and R$_9$ is not benzyl;

provided that when R$_2$, R$_3$, R$_4$, R$_{10}$, R$_{11}$, R$_{12}$ and R$_{13}$ are hydrogen and R$_6$ is

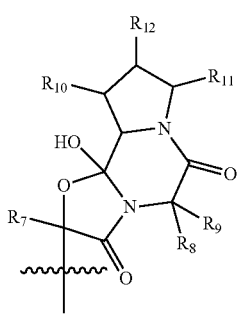

that:

R$_1$ is not allyl;

provided that when R$_1$ is ethyl, R$_5$ is methyl, R$_2$, R$_3$, R$_4$, R$_{10}$, R$_{11}$, R$_{12}$ and R$_{13}$ are hydrogen and R$_6$ is

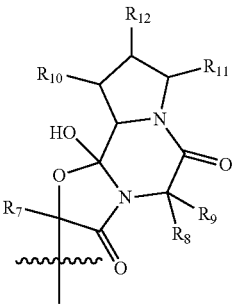

that:

R$_7$ is not isopropyl, R$_8$ is not hydrogen and R$_9$ is not isopropyl;

provided that when R$_1$ is n-propyl, R$_5$ is methyl, R$_2$, R$_3$, R$_4$, R$_{10}$, R$_{11}$, R$_{12}$ and R$_{13}$ is hydrogen and R$_6$ is

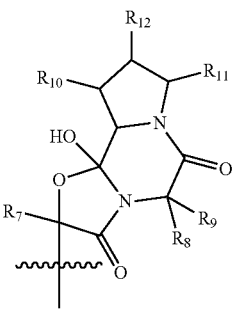

that:

R$_7$ is not isopropyl, R$_8$ is not hydrogen and R$_9$ is not isopropyl provided that when R$_1$ is (C$_1$-C$_4$) alkyl and R$_2$, R$_3$, R$_4$, R$_{10}$, R$_{11}$, R$_{12}$ and R$_{13}$ are hydrogen that:

R$_6$ is not

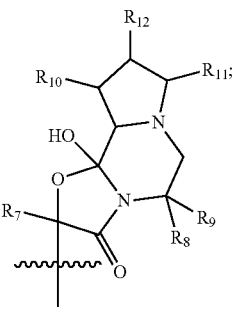

provided that when R$_1$ is CH$_2$NHMe$_2$, R$_5$ is methyl, R$_2$, R$_3$, R$_4$, R$_{10}$, R$_{11}$, R$_{12}$ and R$_{13}$ are hydrogen and R$_6$ is that:
R₇ is not methyl, R₈ is not hydrogen and R₉ is not benzyl;
R₇ is not isopropyl, R₈ is not hydrogen and R₉ is not isopropyl;
R₇ is not isopropyl, R₈ is not hydrogen and R₉ is not benzyl;
R₇ is not isopropyl, R₈ is not hydrogen and R₉ is not isobutyl;
provided that when R₁ is CH₂OCOCH₃, R₅ is methyl, R₂, R₃, R₄, R₁₀, R₁₁, R₁₂ and R₁₃ are hydrogen and R₆ is that:
R₇ is not isopropyl, R₈ is not hydrogen and R₉ is not isobutyl;
R₇ is not isopropyl, R₈ is not hydrogen and R₉ is not isopropyl;
R₇ is not isopropyl, R₈ is not hydrogen and R₉ is not benzyl;
provided that when R₁ is CH₂OH, R₅ is methyl, R₂, R₃, R₄, R₁₀, R₁₁, R₁₂ and R₁₃ are hydrogen and R₆ is that:
R₇ is not isopropyl, R₈ is not hydrogen and R₉ is not isobutyl;
R₇ is not isopropyl, R₈ is not hydrogen and R₉ is not isopropyl;
R₇ is not isopropyl, R₈ is not hydrogen and R₉ is not benzyl;

R₇ is not methyl, R₈ is not hydrogen and R₉ is not benzyl;
provided that when R₁ and R₅ are methyl and R₂, R₃ and R₄ are hydrogen that: R₆ is not provided that when R₁ and R₅ are methyl and R₂, R₃ and R₄ are hydrogen that: R₆ is not provided that when R₁ and R₅ are methyl and R₂, R₃ and R₄ are hydrogen that: R₆ is not In another aspect, the ergoline derivatives described herein include compounds of structural Formula (II):

(II)

or salts, hydrates or solvates thereof wherein:
R₁ is (C₁-C₄) alkyl, substituted (C₁-C₄) alkyl or (C₁-C₄) perfluoroalkyl;

$R_7$ is alkyl, substituted alkyl, acyl, substituted acyl, halo, heteroalkyl, substituted heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$ or —$O_2CR_{107}$;

$R_5$ is hydrogen, ($C_1$-$C_3$) alkyl, substituted ($C_1$-$C_3$) alkyl, or ($C_1$-$C_3$) perfluoroalkyl;

$R_6$ is

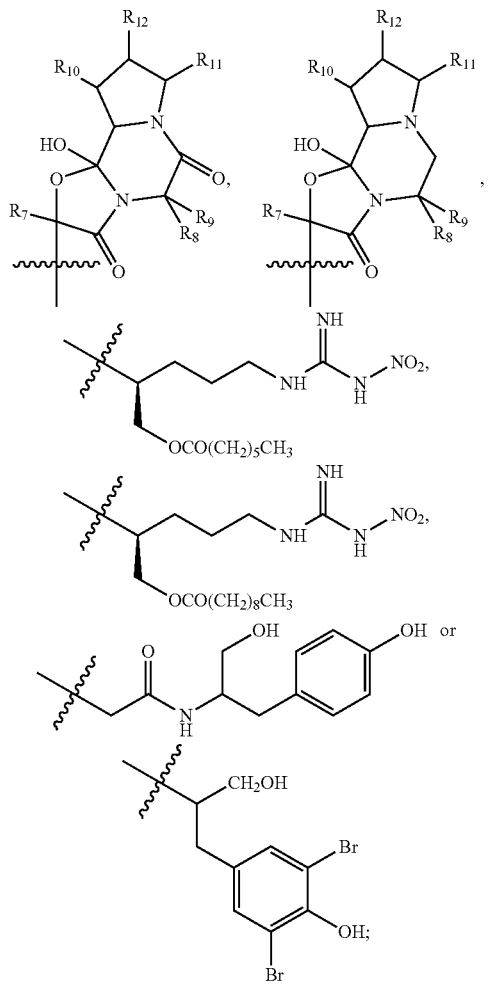

$R_7$ is ($C_1$-$C_4$) alkyl;

$R_8$ is hydrogen, ($C_1$-$C_4$) alkyl, substituted ($C_1$-$C_4$) alkyl, benzyl or substituted benzyl;

$R_9$ is ($C_1$-$C_4$) alkyl or benzyl;

$R_{10}$ is hydrogen, OH, =O, ($C_1$-$C_4$) alkyl, ($C_1$-$C_4$) substituted alkyl, —$CO_2R_{108}$ or —$CONR_{109}R_{110}$;

$R_{11}$ is hydrogen, OH, =O, ($C_1$-$C_4$) alkyl, ($C_1$-$C_4$) substituted alkyl, —$CO_2R_{111}$ or —$CONR_{112}R_{113}$;

$R_{12}$ is hydrogen, OH, =O, ($C_1$-$C_4$) alkyl, ($C_1$-$C_4$) substituted alkyl, —$CO_2R_{414}$ or —$CONR_{115}R_{116}$;

$R_{13}$ is hydrogen or halogen;

$R_{101}$-$R_{116}$ are independently hydrogen, alkyl, substituted alkyl, acyl, substituted acyl, aryl, substituted aryl, arylalkyl, substituted arylalkyl, heteroalkyl, substituted hetereoalkyl, heteroaryl, substituted heteroaryl, heteroarylalkyl or substituted heteroarylalkyl; and k is 0, 1 or 2;

n is 0, 1, 2 or 3;

provided that when $R_1$ and $R_5$ are methyl, $R_2$, $R_{10}$, $R_{11}$, $R_{12}$ and $R_{13}$ are hydrogen and $R_6$ is

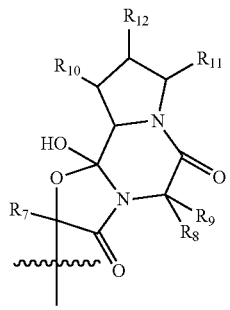

that:

$R_7$ is not methyl, $R_8$ is not hydrogen and $R_9$ is not benzyl;
$R_7$ is not isopropyl, $R_8$ is not hydrogen and $R_9$ is not benzyl;
$R_7$ is not methyl, $R_8$ is not hydrogen and $R_9$ is not isobutyl;
$R_7$ is not methyl, $R_8$ is not hydrogen and $R_9$ is not sec-butyl;
$R_7$ is not isopropyl, $R_8$ is not hydrogen and $R_9$ is not isobutyl;
$R_7$ is not ethyl, $R_8$ is not hydrogen and $R_9$ is not isobutyl;
$R_7$ is not ethyl, $R_8$ is not hydrogen and $R_9$ is not isopropyl;
$R_7$ is not isopropyl, $R_8$ is not hydrogen and $R_9$ is not isopropyl;
$R_7$ is not n-propyl, $R_8$ is not methyl and $R_9$ is not methyl;
$R_7$ is not isopropyl, $R_8$ is not methyl and $R_9$ is not benzyl;
$R_7$ is not ethyl, $R_8$ is not hydrogen and $R_9$ is not benzyl;

provided that when $R_1$ is allyl, $R_5$ is methyl, $R_2$, $R_{10}$, $R_{11}$, $R_{12}$ and $R_{13}$ are hydrogen and $R_6$ is

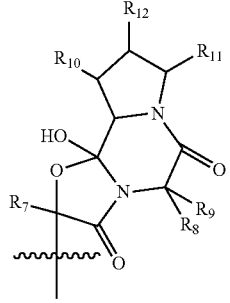

that:

$R_7$ is not methyl, $R_8$ is not hydrogen and $R_9$ is not benzyl;

provided that when $R_1$ is $CH_2OH$, $R_5$ is methyl, $R_2$, $R_{10}$, $R_{11}$, $R_{12}$ and $R_{13}$ are hydrogen and $R_6$ is

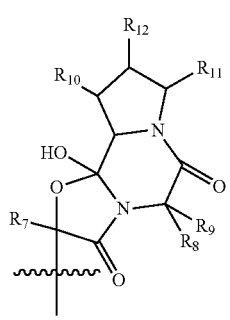

that:

$R_7$ is not methyl, $R_8$ is not hydrogen and $R_9$ is not benzyl;

provided that when $R_1$ is $CH_2OH$, $R_5$ is methyl, $R_2$, $R_{10}$, $R_{11}$, and $R_{12}$ are hydrogen, $R_{13}$ is bromine and $R_6$ is

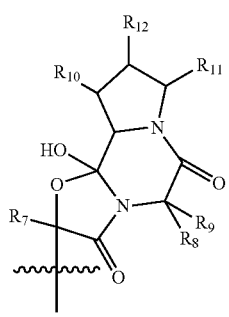

that:

$R_7$ is not isopropyl, $R_8$ is not hydrogen and $R_9$ is not sec-butyl.

Also provided are derivatives, including salts, esters, enol ethers, enol esters, solvates, hydrates and prodrugs of the compounds described herein. Further provided are compositions containing the compounds provided herein and a vehicle.

Methods of treating, preventing, or ameliorating medical disorders such as, for example, migraine, ALS, Parkinson's disease, extra-pyramidal disorders, depression, nausea, restless legs syndrome, insomnia, aggression, Huntington's disease, dystonia, parsomnia and hyperlactinemia are also provided herein. In practicing the methods, effective amounts of the compounds or compositions containing therapeutically effective concentrations of the compounds are administered.

Methods of antagonizing receptors such as, for example, 5-$HT_{2A}$, 5-$HT_{2B}$, 5-$HT_3$ serotonin, D2 and D3 dopamine and A1 and A2 adrenergic receptors are also provided herein. In practicing the methods, effective amounts of the compounds or compositions are administered.

Methods of agonizing receptors such as, for example, 5-$HT_{1D}$, 5-$HT_{1B}$, 5-$HT_{1F}$ serotonin receptors are also provided herein. In practicing the methods, effective amounts of the compounds or compositions are administered.

Methods of regulating serotonin transport are also provided herein. In practicing the methods, effective amounts of the compounds or compositions are administered.

Methods of making a compound of structural formula (III) wherein $R_1$ is benzyl, methyl, ethyl, n-propyl, isopropyl, n-butyl, isobutyl or allyl are also provided herein.

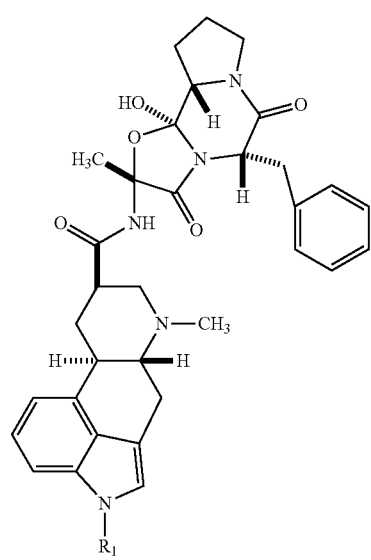

(III)

The method comprises contacting dihydroergotamine with alkaline metal in an organic solvent or a mixture of organic solvents to form a solution and contacting this solution with a halide selected from the group consisting of benzyl halide, methyl halide, ethyl halide, n-propyl halide, isopropyl halide, n-butyl halide, isobutyl halide, sec-butyl halide and allyl halide.

DETAILED DESCRIPTION

Definitions

Figure 1:
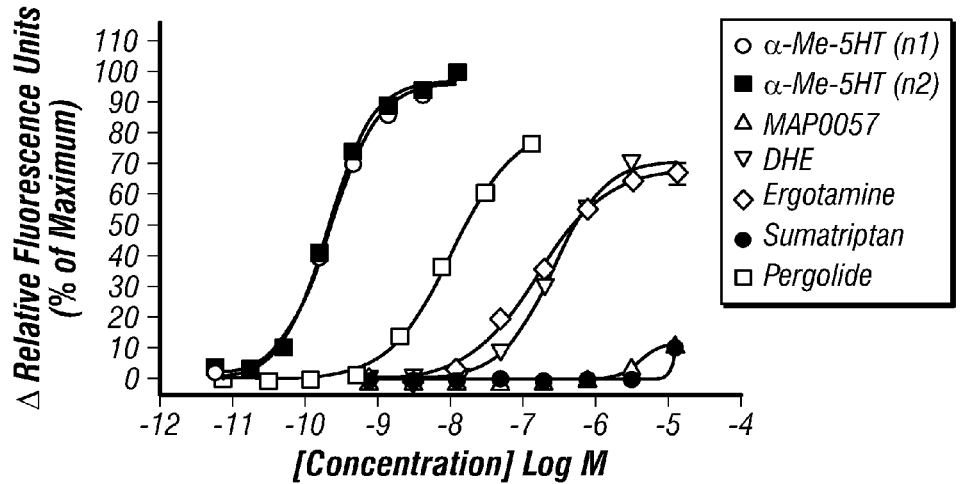
FIG. 1 illustrates the inability of 1-methyl-dihydroergotamine to agonize the 5-$HT_{2B}$ receptor and provides a comparison to known agonists of the 5-$HT_{2B}$ receptor.

Unless defined otherwise, all technical and scientific terms used herein have the same meaning as is commonly understood by one of ordinary skill in the art to which this invention belongs. In the event that there are a plurality of definitions for a term herein, those in this section prevail unless stated otherwise.

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl).

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkoxy," by itself or as part of another substituent, refers to a radical of the formula —O—$R^{400}$, where $R^{400}$ is alkyl or substituted alkyl as defined herein.

"Acyl" by itself or as part of another substituent refers to a radical —C(O)$R^{401}$, where $R^{401}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6$-$C_{20}$ aryl). In other embodiments, an aryl group comprises from 6 to 15 carbon atoms ($C_6$-$C_{15}$ aryl). In still other embodiments, an aryl group comprises from 6 to 15 carbon atoms ($C_6$-$C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6$-$C_{30}$) arylalkyl, e.g., the alkanyl, alkenyl or alkynyl moiety of the arylalkyl group is ($C_1$-$C_{10}$) alkyl and the aryl moiety is ($C_6$-$C_{20}$) aryl. In other embodiments, an arylalkyl group is ($C_6$-$C_{20}$) arylalkyl, e.g., the alkanyl, alkenyl or alkynyl moiety of the arylalkyl group is ($C_1$-$C_8$) alkyl and the aryl moiety is ($C_6$-$C_{12}$) aryl. In still other embodiments, an arylalkyl group is ($C_6$-$C_{15}$) arylalkyl, e.g., the alkanyl, alkenyl or alkynyl moiety of the arylalkyl group is ($C_1$-$C_5$) alkyl and the aryl moiety is ($C_6$-$C_{10}$) aryl.

"Compounds" refers to compounds encompassed by structural formulae disclosed herein and includes any specific compounds within these formulae whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated or unhydrated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, O—S—, —N$R^{501}R^{502}$—, =N—N=, —N=N—, —N=N—N$R^{503}R^{404}$, —P$R^{505}$—, —P(O)$_2$—, —PO$R^{506}$—, —O—P(O)$_2$—, —SO—, —SO$_2$—, —Sn$R^{507}R^{508}$— and the like, where $R^{501}$, $R^{502}$, $R^{503}$, $R^{504}$, $R^{505}$, $R^{506}$, $R^{507}$ and $R^{508}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group.

Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"Parent Aromatic Ring System" refers to an unsaturated cyclic or polycyclic ring system having a conjugated it electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). The application of a therapeutic for preventing or prevention of a disease of disorder is known as 'prophylaxis.' In some embodiments, the compounds provided herein provide superior prophylaxis because of lower long term side effects over long time periods.

"Protecting group" refers to a grouping of atoms that when attached to a reactive functional group in a molecule masks, reduces or prevents reactivity of the functional group during chemical synthesis. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilylethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —$NR^cR^c$ is meant to include —$NH_2$, —NH-alkyl, N-pyrrolidinyl and N-morpholinyl.

Similarly, substituent groups useful for substituting unsaturated carbon atoms in the specified group or radical include, but are not limited to, —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_{2O}$, —$S(O)_2OR^b$, —$OS(O)_2R^b$, —$OS(O)_2O^-$, —$S(O)_2OR^b$, —$P(O)(O^-)_2$, —$P(O)(OR^b)(O)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups useful for substituting nitrogen atoms in heteroalkyl and cycloheteroalkyl groups include, but are not limited to, —$R^a$, —$O^-$, —$OR^b$, —$SR^b$, —$S^-$, —$NR^cR^c$, trihalomethyl, —$CF_3$, —CN, —NO, —$NO_2$, —$S(O)_2R^b$, —$S(O)_2O^-$, —$S(O)_2OR^b$, —$OS(O)_2R^b$, —$OS(O)_2O^-$, —$O(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)OR^b$, —$C(S)OR^b$, $C(O)NR^cR^c$, —$C(NR^b)NR^cR^c$, —$OC(O)R^b$, —$OC(S)R^b$, —$OC(O)OR^b$, —$OC(S)OR^b$, —$NR^bC(O)R^b$, —$NR^bC(S)R^b$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$, $R^b$ and $R^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Subject," "individual" or "patient" is used interchangeably herein and refers to a vertebrate, preferably a mammal. Mammals include, but are not limited to, murines, rodents, simians, humans, farm animals, sport animals and pets.

"Treating" or "treatment" of any disease or disorder refers, in some embodiments, to ameliorating the disease or disorder (i.e., arresting or reducing the development of the disease or at least one of the clinical symptoms thereof,). Treatment may also be considered to include preemptive or prophylactic administration to ameliorate, arrest or prevent the development of the disease or at least one of the clinical symptoms. In a further feature the treatment rendered has lower potential for longterm side effects over multiple years. In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, adsorption, distribution, metabolism and excretion etc., of the patient to be treated.

"Vehicle" refers to a diluent, excipient or carrier with which a compound is administered to a subject.

B. Compounds

The compounds described herein include compounds of structural formula (I):

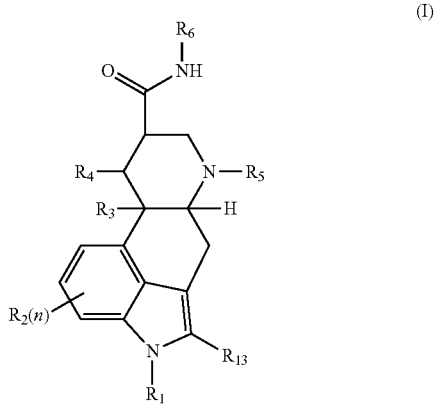

(I)

or salts, hydrates or solvates thereof wherein:

$R_1$ is ($C_1$-$C_4$) alkyl, substituted ($C_1$-$C_4$) alkyl or ($C_1$-$C_4$) perfluoroalkyl;

$R_2$ is alkyl, substituted alkyl, acyl, substituted acyl, halo, heteroalkyl, substituted heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$ or —$O_2CR_{107}$;

$R_3$ and $R_4$ are independently hydrogen, deuterium, fluoro, hydroxy or methoxy;

$R_5$ is hydrogen, ($C_1$-$C_3$) alkyl, substituted ($C_1$-$C_4$) alkyl or ($C_1$-$C_3$) perfluoroalkyl;

$R_6$ is

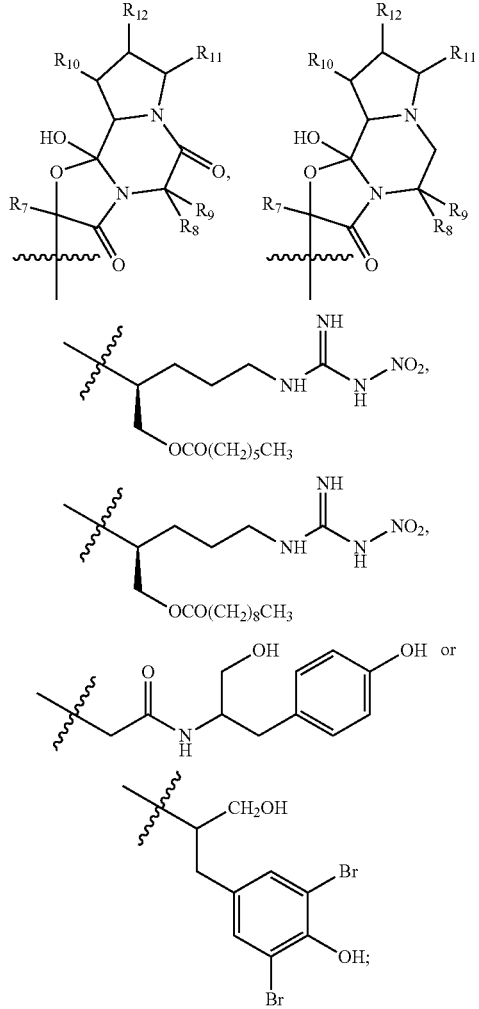

$R_7$ is $(C_1$-$C_4)$ alkyl;
$R_8$ is hydrogen, $(C_1$-$C_4)$ alkyl, substituted $(C_1$-$C_4)$ alkyl, benzyl or substituted benzyl;
$R_9$ is $(C_1$-$C_4)$ alkyl or benzyl;
$R_{10}$ is hydrogen, OH, =O, $(C_1$-$C_4)$ alkyl, $(C_1$-$C_4)$ substituted alkyl, —$CO_2R_{108}$ or —$CONR_{109}R_{110}$;
$R_{11}$ is hydrogen, OH, =O, $(C_1$-$C_4)$ alkyl, $(C_1$-$C_4)$ substituted alkyl, —$CO_2R_{111}$ or —$CONR_{112}R_{113}$,
$R_{12}$ is hydrogen, OH, =O, $(C_1$-$C_4)$ alkyl, $(C_1$-$C_4)$ substituted alkyl, —$CO_2R_{114}$ or —$CONR_{115}R_{116}$;
$R_{13}$ is hydrogen or halogen;
$R_{101}$-$R_{116}$ are independently hydrogen, alkyl, substituted alkyl, acyl, substituted acyl, aryl, substituted aryl, arylalkyl, substituted arylalkyl, heteroalkyl, substituted hetereoalkyl, heteroaryl, substituted heteroaryl, heteroarylalkyl or substituted heteroarylalkyl; and
k is 0, 1 or 2;
n is 0, 1, 2 or 3;
provided that when $R_1$ and $R_5$ are methyl, $R_2$, $R_3$, $R_4$, $R_{10}$, $R_{11}$, $R_{12}$ and $R_{13}$ are hydrogen and $R_6$ is

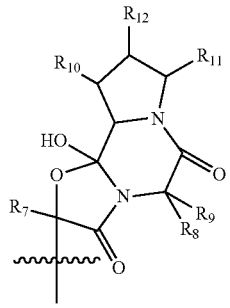

that:
$R_7$ is not methyl, $R_8$ is not hydrogen and $R_9$ is not sec-butyl;
$R_7$ is not methyl, $R_8$ is not hydrogen and $R_9$ is not benzyl;
$R_7$ is not n-butyl, $R_8$ is not methyl and $R_9$ is not methyl;
$R_7$ is not isopropyl, $R_8$ is not methyl and $R_9$ is not benzyl;
$R_7$ is not isopropyl, $R_8$ is not hydrogen and $R_9$ is not n-propyl;
$R_7$ is not isopropyl, $R_8$ is not hydrogen and $R_9$ is not isobutyl;
$R_7$ is not isopropyl, $R_8$ is not hydrogen and $R_9$ is not isopropyl;
$R_7$ is not ethyl, $R_8$ is not hydrogen and $R_9$ is not isobutyl;
provided that when $R_1$ and $R_5$ are methyl, $R_3$ is —OH, $R_2$, $R_4$, $R_{10}$, $R_{11}$, $R_{12}$ and $R_{13}$ are hydrogen and $R_6$ is

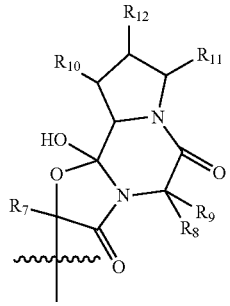

that:
$R_7$ is not methyl, $R_8$ is not hydrogen and $R_9$ is not sec-butyl;
provided that when $R_1$ and $R_5$ are methyl, $R_3$ is —$OCH_3$, $R_2$, $R_4$, $R_{10}$, $R_{11}$, $R_{12}$ and $R_{13}$ are hydrogen and $R_6$ is

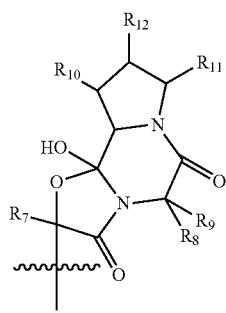

that:
$R_7$ is not methyl, $R_8$ is not hydrogen and $R_9$ is not sec-butyl;
$R_7$ is not isopropyl, $R_8$ is not hydrogen and $R_9$ is not isopropyl;
$R_7$ is not isopropyl, $R_8$ is not hydrogen and $R_9$ is not benzyl;

$R_7$ is not methyl, $R_8$ is not hydrogen and $R_9$ is not benzyl;
$R_7$ is not methyl, $R_8$ is not hydrogen and $R_9$ is not sec-butyl;
provided that when $R_1$ and $R_5$ are methyl, $R_2$, $R_3$, $R_4$, $R_{10}$, $R_{11}$ and $R_{12}$ are hydrogen, $R_{13}$ is bromine and $R_6$ is

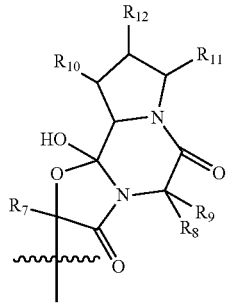

that:
$R_7$ is not methyl, $R_8$ is not hydrogen and $R_9$ is not benzyl;
$R_7$ is not methyl, $R_8$ is not hydrogen and $R_9$ is not isopropyl;
$R_7$ is not isopropyl, $R_8$ is not hydrogen and $R_9$ is not isopropyl;
$R_7$ is not isopropyl, $R_8$ is not hydrogen and $R_9$ is not isobutyl;
provided that when $R_1$ is n-propyl, $R_5$ is methyl, $R_2$, $R_3$, $R_4$, $R_{10}$, $R_{11}$ and $R_{12}$ are hydrogen, $R_{13}$ is bromine and $R_6$ is

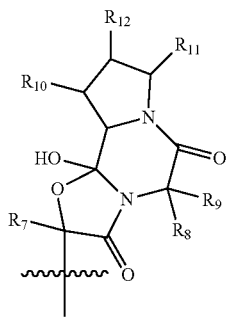

that:
$R_7$ is not isopropyl, $R_8$ is not hydrogen and $R_9$ is not isopropyl;
provided that when $R_1$ and $R_5$ are methyl, $R_2$, $R_3$, $R_4$, $R_{10}$, $R_{11}$ and $R_{12}$ are hydrogen, $R_{13}$ is iodine and $R_6$ is

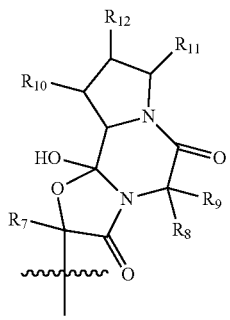

that:
$R_7$ is not methyl, $R_8$ is not hydrogen and $R_9$ is not benzyl;
provided that when $R_1$ is methyl, $R_5$ is n-propyl, $R_2$, $R_3$, $R_4$, $R_{10}$, $R_{11}$, $R_{12}$ and $R_{13}$ are hydrogen and $R_6$ is

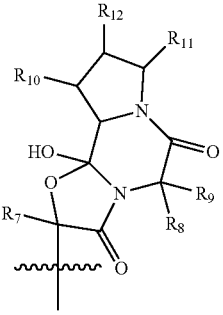

that:
$R_7$ is not isopropyl, $R_8$ is not hydrogen and $R_9$ is not benzyl;
$R_7$ is not methyl, $R_8$ is not hydrogen and $R_9$ is not benzyl;
provided that when $R_2$, $R_3$, $R_4$, $R_{10}$, $R_{11}$, $R_{12}$ and $R_{13}$ are hydrogen and $R_6$ is

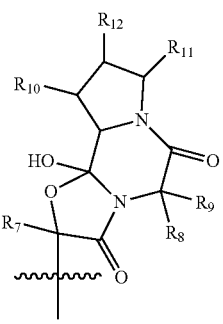

that:
$R_1$ is not allyl;
provided that when $R_1$ is ethyl, $R_5$ is methyl, $R_2$, $R_3$, $R_4$, $R_{10}$, $R_{11}$, $R_{12}$ and $R_{13}$ are hydrogen and $R_6$ is

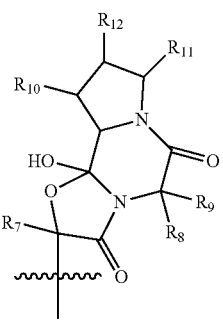

that:
$R_7$ is not isopropyl, $R_8$ is not hydrogen and $R_9$ is not isopropyl;
provided that when $R_1$ is n-propyl, $R_5$ is methyl, $R_2$, $R_3$, $R_4$, $R_{10}$, $R_{11}$, $R_{12}$ and $R_{13}$ is hydrogen and $R_6$ is

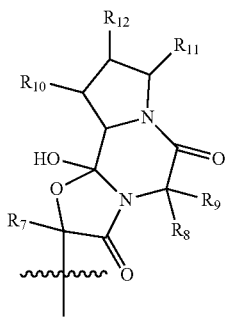

that:

$R_7$ is not isopropyl, $R_8$ is not hydrogen and $R_9$ is not isopropyl provided that when $R_1$ is $(C_1-C_4)$ alkyl and $R_2$, $R_3$, $R_4$, $R_{10}$, $R_{11}$, $R_{12}$ and $R_{13}$ are hydrogen that:

$R_6$ is not

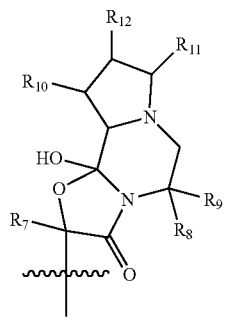

provided that when $R_1$ is $CH_2NHMe_2$, $R_5$ is methyl, $R_2$, $R_3$, $R_4$, $R_{10}$, $R_{11}$, $R_{12}$ and $R_{13}$ are hydrogen and $R_6$ is

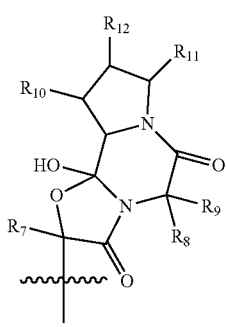

that:

$R_7$ is not methyl, $R_8$ is not hydrogen and $R_9$ is not benzyl;

$R_7$ is not isopropyl, $R_8$ is not hydrogen and $R_9$ is not isopropyl;

$R_7$ is not isopropyl, $R_8$ is not hydrogen and $R_9$ is not benzyl;

$R_7$ is not isopropyl, $R_8$ is not hydrogen and $R_9$ is not isobutyl;

provided that when $R_1$ is $CH_2OCOCH_3$, $R_5$ is methyl, $R_2$, $R_3$, $R_4$, $R_{10}$, $R_{11}$, $R_{12}$ and $R_{13}$ are hydrogen and $R_6$ is

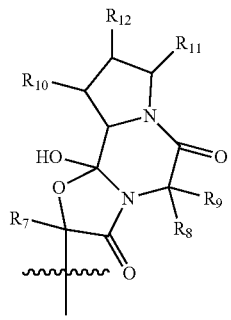

that:

$R_7$ is not isopropyl, $R_8$ is not hydrogen and $R_9$ is not isobutyl;

$R_7$ is not isopropyl, $R_8$ is not hydrogen and $R_9$ is not isopropyl;

$R_7$ is not isopropyl, $R_8$ is not hydrogen and $R_9$ is not benzyl;

provided that when $R_1$ is $CH_2OH$, $R_5$ is methyl, $R_2$, $R_3$, $R_4$, $R_{10}$, $R_{11}$, $R_{12}$ and $R_{13}$ are hydrogen and $R_6$ is

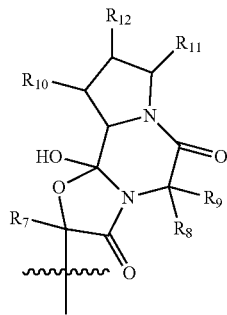

that:

$R_7$ is not isopropyl, $R_8$ is not hydrogen and $R_9$ is not isobutyl;

$R_7$ is not isopropyl, $R_8$ is not hydrogen and $R_9$ is not isopropyl;

$R_7$ is not isopropyl, $R_8$ is not hydrogen and $R_9$ is not benzyl;

$R_7$ is not methyl, $R_8$ is not hydrogen and $R_9$ is not benzyl;

provided that when $R_1$ and $R_5$ are methyl and $R_2$, $R_3$ and $R_4$ are hydrogen that: $R_6$ is not

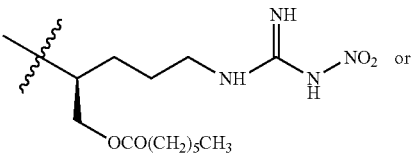

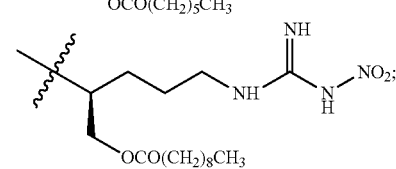

provided that when $R_1$ and $R_5$ are methyl and $R_2$, $R_3$ and $R_4$ are hydrogen that: $R_6$ is not

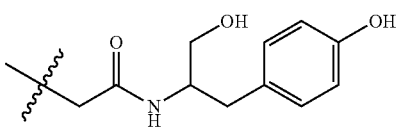 [SMILES: *CC(=O)NC(CO)Cc1ccc(O)cc1]

provided that when $R_1$ and $R_5$ are methyl and $R_2$, $R_3$ and $R_4$ are hydrogen that: $R_6$ is not

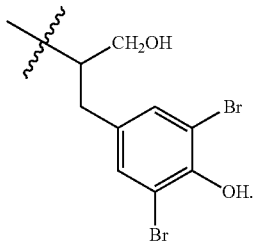 [SMILES: *C(CO)Cc1cc(Br)c(O)c(Br)c1]

In some embodiments, $R_1$ is $(C_1\text{-}C_3)$ alkyl, $(C_1\text{-}C_3)$ substituted alkyl or $(C_1\text{-}C_3)$ perfluoroalkyl. In other embodiments, $R_1$ is $(C_1\text{-}C_4)$ alkyl or $(C_1\text{-}C_4)$ perfluoroalkyl. In still other embodiments, $R_1$ is —$CH_3$, —$C_2H_5$, —$C_3H_7$, i-$C_3H_7$, —$CF_3$, —$C_2F_5$, —$C_3F_7$ or i-$C_3F_7$. In still other embodiments, $R_1$ is —$CH_3$, —$C_2H_5$, —$C_3H_7$, —$CF_3$, —$C_2F_5$ or —$C_3F_7$.

In some embodiments, $R_2$ is $(C_1\text{-}C_4)$ alkyl, $(C_1\text{-}C_4)$ substituted alkyl, $(C_1\text{-}C_4)$ acyl, $(C_1\text{-}C_4)$ substituted acyl, halo, $(C_1\text{-}C_4)$ heteroalkyl, $(C_1\text{-}C_4)$ substituted heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$ or —$O_2CR_{107}$. In other embodiments, $R_2$ is $(C_1\text{-}C_4)$ alkyl, $(C_1\text{-}C_4)$ substituted alkyl, $(C_1\text{-}C_4)$ acyl, $(C_1\text{-}C_4)$ substituted acyl, halo, —$NO_2$, —$OR_{101}$, —$NR_{102}R_{103}$, —$CONR_{104}R_{105}$, —$CO_2R_{106}$ or —$O_2CR_{107}$. In still other embodiments, $R_2$ is $(C_1\text{-}C_2)$ alkyl, $(C_1\text{-}C_2)$ substituted alkyl, halo, —$NO_2$, $OR_{101}$, —$NR_{102}R_{103}$, —$CONR_{104}R_{105}$, —$CO_2R_{106}$ or —$O_2CR_{107}$.

In some embodiments, n is 0 or 1. In other embodiments, n is 0.

In some embodiments, $R_4$ is hydrogen. In other embodiments, $R_3$ and $R_4$ are hydrogen. In still other embodiments, $R_3$ and $R_4$ are deuterium.

In some embodiments, $R_5$ is —$CH_3$, —$C_2H_5$, —$C_3H_7$, —$CF_3$, —$C_2F_5$ or —$C_3F_7$. In other embodiments, $R_5$ is —$CH_3$ or —$CF_3$.

In some embodiments, $R_6$ is

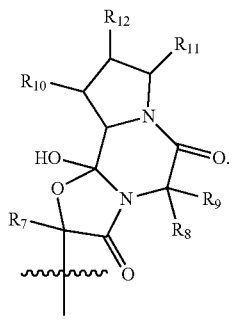

In some embodiments, $R_7$ is methyl, ethyl or isopropyl. In other embodiments, $R_8$ is hydrogen or methyl. In still other embodiments, $R_9$ is n-propyl, isopropyl, sec-butyl, isobutyl or benzyl. In some embodiments, $R_{10}$, $R_{11}$ and $R_{12}$ are independently hydrogen, OH or $(C_1\text{-}C_4)$ alkyl. In other embodiments, $R_{10}$, $R_{11}$ and $R_{12}$ are hydrogen.

In some embodiments, $R_{13}$ is hydrogen or bromine.

In some embodiments, $R_1$ is $(C_1\text{-}C_4)$ alkyl or $(C_1\text{-}C_4)$ perfluoroalkyl and $R_{13}$ is hydrogen or bromine. In other embodiments, $R_1$ is —$CH_3$, —$C_2H_5$, —$C_3H_7$, —$CF_3$, —$C_2F_5$, —$C_3F_7$ or i-$C_3F_7$ and $R_{13}$ is hydrogen or bromine.

In some embodiments, $R_1$ is $(C_1\text{-}C_4)$ alkyl or $(C_1\text{-}C_4)$ perfluoroalkyl and $R_6$ is

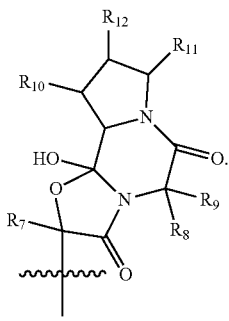

In some of these embodiments, $R_7$ is methyl, ethyl or isopropyl, $R_8$ is hydrogen or methyl, $R_9$ is n-propyl, isopropyl, sec-butyl, isobutyl or benzyl. In some of the above embodiments, $R_{10}$, $R_{11}$ and $R_{12}$ are independently hydrogen, OH or $(C_1\text{-}C_4)$ alkyl. In still other of the above embodiments, $R_{10}$, $R_{11}$ and $R_{12}$ are hydrogen. In still other of the above embodiments, $R_2$ is $(C_1\text{-}C_2)$ alkyl, $(C_1\text{-}C_2)$ substituted alkyl, halo, —$NO_2$, —$OR_{101}$, —$NR_{102}R_{103}$, —$CONR_{104}R_{105}$, —$CO_2R_{106}$ or —$O_2CR_{107}$. In still other of the above embodiments, n is 0 or 1. In still other of the above embodiments, n is 0. In still other of the above embodiments, $R_3$ and $R_4$ are deuterium. In still other of the above embodiments, n is 0. In still other of the above embodiments, $R_3$ and $R_4$ are hydrogen.

In some embodiments, $R_1$ is —$CH_3$, —$C_2H_5$, —$C_3H_7$, —$CF_3$, —$C_2F_5$, —$C_3F_7$ or i-$C_3F_7$ and $R_6$ is

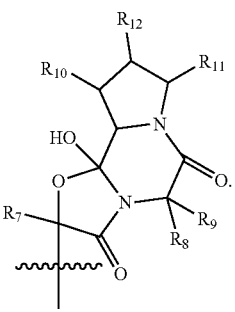

In some of these embodiments, $R_7$ is methyl, ethyl or isopropyl, $R_8$ is hydrogen or methyl, $R_9$ is n-propyl, isopropyl, sec-butyl, isobutyl or benzyl. In some of the above embodiments, $R_{10}$, $R_{11}$ and $R_{12}$ are independently hydrogen, OH or $(C_1\text{-}C_4)$ alkyl. In still other of the above embodiments, $R_{10}$, $R_{11}$ and $R_{12}$ are hydrogen. In still other of the above embodiments, $R_2$ is $(C_1\text{-}C_2)$ alkyl, $(C_1\text{-}C_2)$ substituted alkyl, halo, —$NO_2$, —$OR_{101}$, —$NR_{102}R_{103}$, —$CONR_{104}R_{1015}$, —$CO_2R_{106}$ or —$O_2CR_{107}$. In still other of the above embodiments, n is 0 or 1. In still other of the above embodiments, n is 0. In still other of the above embodiments, $R_3$ and $R_4$ are deuterium. In still other of the above embodiments, n is 0. In still other of the above embodiments, $R_3$ and $R_4$ are hydrogen.

In some embodiments of a compound of Formula (I): $R_1$ is —$CH_3$, —$C_2H_5$, —$C_3H_7$, i-$C_3H_7$, —$CF_3$, —$C_2F_5$, —$C_3F_7$ or i-$C_3F_7$, $R_2$ is ($C_1$-$C_4$) alkyl, ($C_1$-$C_4$) substituted alkyl, ($C_1$-$C_4$) acyl, ($C_1$-$C_4$) substituted acyl, halo, —$NO_2$, —$OR^{101}$, —$NR_{102}R_{103}$, —$CONR_{104}R_{105}$, —$CO_2R_{106}$ or —$O_2CR_{107}$, n is 0 or 1, $R_3$ and $R_4$ are independently hydrogen or deuterium, $R_5$ is —$CH_3$, —$C_2H_5$, —$C_3H_7$, —$CF_3$, $C_2F_5$ or —$C_3F_7$, $R_6$ is

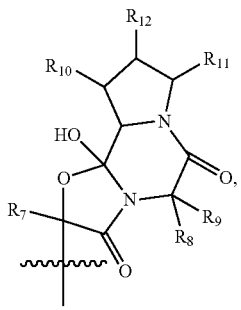

$R_{10}$, $R_{11}$ and $R_{12}$ are independently hydrogen, OH or ($C_1$-$C_4$) alkyl; and $R_{13}$ is hydrogen or bromine In other embodiments of a compound of Formula (I), $R_1$ is $CH_3$, —$C_2H_5$, -n$C_3H_7$, —$CF_3$, $C_2F_5$ or -n$C_3F_7$, $R_2$ is $C_1$-$C_2$) alkyl, ($C_1$-$C_2$) substituted alkyl, halo, —$NO_2$, —$NR_{102}R_{103}$, —$CONR_{104}R_{105}$, —$CO_2R_{106}$ or —$O_2CR_{107}$, n is 0; $R_3$ and $R_4$ are independently hydrogen or deuterium, $R_5$ is —$CH_3$ or —$CF_3$, $R_6$ is

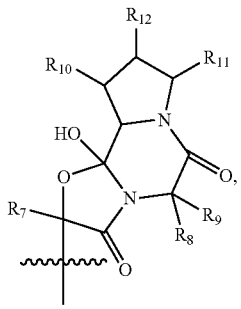

$R_7$ is methyl, ethyl or isopropyl, $R_8$ is hydrogen or methyl, $R_9$ is n-propyl, isopropyl, sec-butyl, isobutyl or benzyl, $R_{10}$, $R_{11}$ and $R_{12}$ are hydrogen; and $R_{13}$ is hydrogen.

The compounds described herein include compounds of structural formula (II):

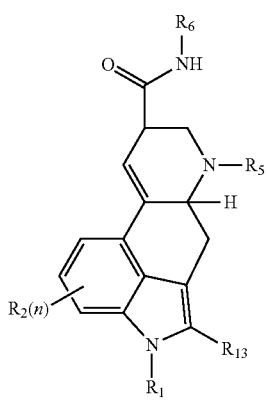

(II)

or salts, hydrates or solvates thereof wherein:

$R_1$ is ($C_1$-$C_4$) alkyl, substituted ($C_1$-$C_4$) alkyl or ($C_1$-$C_4$) perfluoroalkyl;

$R_2$ is alkyl, substituted alkyl, acyl, substituted acyl, halo, heteroalkyl, substituted heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$ or —$O_2CR_{107}$;

$R_5$ is hydrogen, ($C_1$-$C_3$) alkyl, substituted ($C_1$-$C_3$) alkyl, or ($C_1$-$C_3$) perfluoroalkyl;

$R_6$ is

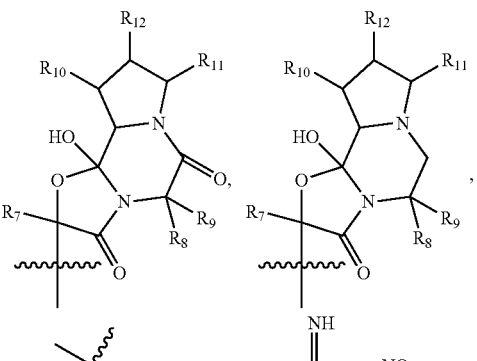

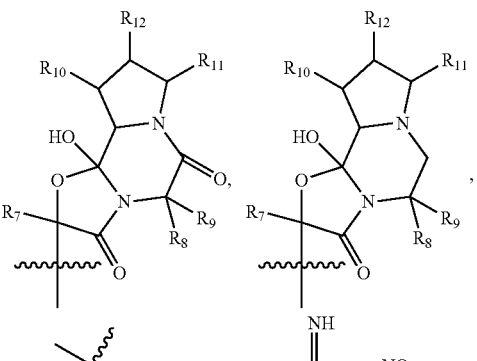

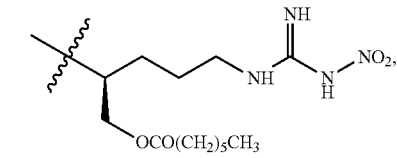

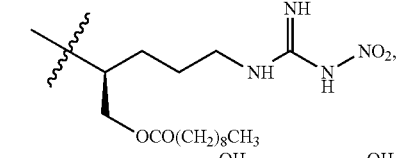

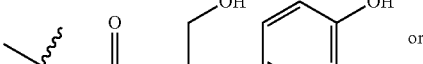

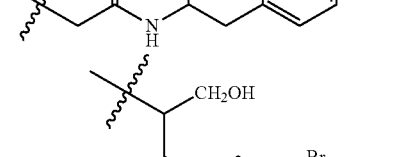

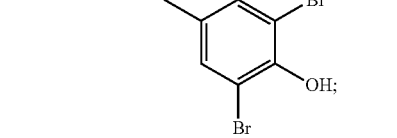

$R_7$ is ($C_1$-$C_4$) alkyl;

$R_8$ is hydrogen, ($C_1$-$C_4$) alkyl, substituted ($C_1$-$C_4$) alkyl, benzyl or substituted benzyl;

$R_9$ is ($C_1$-$C_4$) alkyl or benzyl;

$R_{10}$ is hydrogen, OH, =O, ($C_1$-$C_4$) alkyl, ($C_1$-$C_4$) substituted alkyl, —$CO_2R_{108}$ or —$CONR_{109}R_{110}$;

$R_{11}$ is hydrogen, OH, =O, ($C_1$-$C_4$) alkyl, ($C_1$-$C_4$) substituted alkyl, —$CO_2R_{111}$ or —$CONR_{112}R_{113}$;

$R_{12}$ is hydrogen, OH, =O, ($C_1$-$C_4$) alkyl, ($C_1$-$C_4$) substituted alkyl, —$CO_2R_{114}$ or —$CONR_{115}R_{116}$;

$R_{13}$ is hydrogen or halogen;

$R_{101}$-$R_{116}$ are independently hydrogen, alkyl, substituted alkyl, acyl, substituted acyl, aryl, substituted aryl, arylalkyl, substituted arylalkyl, heteroalkyl, substituted hetereoalkyl, heteroaryl, substituted heteroaryl, heteroarylalkyl or substituted heteroarylalkyl; and k is 0, 1 or 2;

n is 0, 1, 2 or 3;

provided that when $R_1$ and $R_5$ are methyl, $R_2$, $R_{10}$, $R_{11}$, $R_{12}$ and $R_{13}$ are hydrogen and $R_6$ is

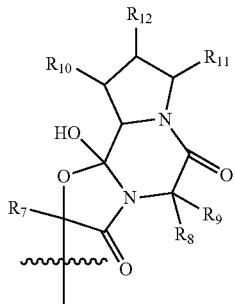

that:
$R_7$ is not methyl, $R_8$ is not hydrogen and $R_9$ is not benzyl;
$R_7$ is not isopropyl, $R_8$ is not hydrogen and $R_9$ is not benzyl;
$R_7$ is not methyl, $R_8$ is not hydrogen and $R_9$ is not isobutyl;
$R_7$ is not methyl, $R_8$ is not hydrogen and $R_9$ is not sec-butyl;
$R_7$ is not isopropyl, $R_8$ is not hydrogen and $R_9$ is not isobutyl;
$R_7$ is not ethyl, $R_8$ is not hydrogen and $R_9$ is not isobutyl;
$R_7$ is not ethyl, $R_8$ is not hydrogen and $R_9$ is not isopropyl;
$R_7$ is not isopropyl, $R_8$ is not hydrogen and $R_9$ is not isopropyl;
$R_7$ is not n-propyl, $R_8$ is not methyl and $R_9$ is not methyl;
$R_7$ is not isopropyl, $R_8$ is not methyl and $R_9$ is not benzyl;
$R_7$ is not ethyl, $R_8$ is not hydrogen and $R_9$ is not benzyl;
provided that when $R_1$ is allyl, $R_5$ is methyl, $R_2$, $R_{11}$, $R_{12}$ and $R_{13}$ are hydrogen and $R_6$ is

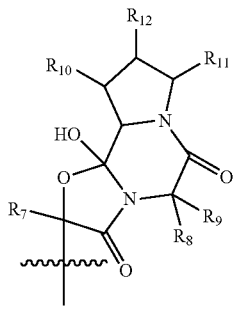

that:
$R_7$ is not methyl, $R_8$ is not hydrogen and $R_9$ is not benzyl;
provided that when $R_1$ is $CH_2OH$, $R_5$ is methyl, $R_2$, $R_{10}$, $R_{11}$, $R_{12}$ and $R_{13}$ are hydrogen and $R_6$ is

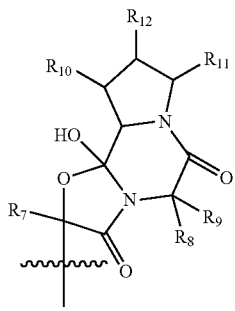

that:
$R_7$ is not methyl, $R_8$ is not hydrogen and $R_9$ is not benzyl;
provided that when $R_1$ is $CH_2OH$, $R_5$ is methyl, $R_2$, $R_{10}$, $R_{11}$, and $R_{12}$ are hydrogen, $R_{13}$ is bromine and $R_6$ is

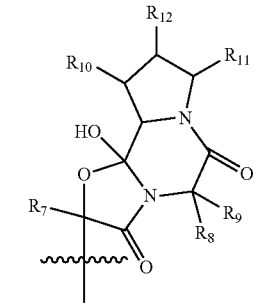

that:
$R_7$ is not isopropyl, $R_8$ is not hydrogen and $R_9$ is not sec-butyl.

In some embodiments, $R_1$ is $(C_1$-$C_3)$ alkyl, $(C_1$-$C_3)$ substituted alkyl or $(C_1$-$C_3)$ perfluoroalkyl. In other embodiments, $R_1$ is $(C_1$-$C_4)$ alkyl or $(C_1$-$C_4)$ perfluoroalkyl. In still other embodiments, $R_1$ is —$CH_3$, —$C_2H_5$, —$C_3H_2$, i-$C_3H_7$, —$CF_3$, —$C_2F_5$, —$C_3F_7$ or i-$C_3F_7$. In still other embodiments, $R_1$ is $CH_3$, —$C_2H_5$, —$C_3H_7$, —$CF_3$, $C_2F_5$ or —$C_3F_7$.

In some embodiments, $R_2$ is $(C_1$-$C_4)$ alkyl, $(C_1$-$C_4)$ substituted alkyl, $(C_1$-$C_4)$ acyl, $(C_1$-$C_4)$ substituted acyl, halo, $(C_1$-$C_4)$ heteroalkyl, $(C_1$-$C_4)$ substituted heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$ or —$O_2CR_{107}$. In other embodiments, $R_2$ is $(C_1$-$C_4)$ alkyl, $(C_1$-$C_4)$ substituted alkyl, $(C_1$-$C_4)$ acyl, $(C_1$-$C_4)$ substituted acyl, halo, —$NO_2$, —$OR_{101}$—$NR_{102}R_{103}$, —$CONR_{104}R_{105}$, —$CO_2R_{106}$ or —$O_2CR_{102}$. In still other embodiments, $R_2$ is $(C_1$-$C_2)$ alkyl, $(C_1$-$C_2)$ substituted alkyl, halo, —$NO_2$, —$NO_2R_{101}$, —$NR_{102}R_{103}$, —$CONR_{104}R_{105}$, —$CO_2R_{106}$ or —$O_2CR_{107}$.

In some embodiments, n is 0 or 1. In other embodiments, n is 0.

In some embodiments, $R_5$ is —$CH_3$, —$C_2H_5$, —$C_3H_7$, —$CF_3$, $C_2F_5$ or —$C_3F_7$. In other embodiments, $R_5$ is —$CH_3$ or —$CF_3$.

In some embodiments, $R_6$ is

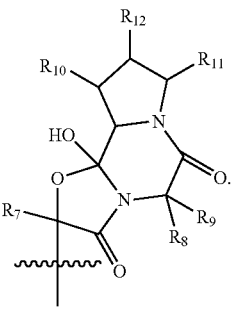

In some embodiments, $R_7$ is methyl, ethyl or isopropyl. In other embodiments, $R_8$ is hydrogen or methyl. In still other embodiments, $R_9$ is n-propyl, isopropyl, sec-butyl, isobutyl or benzyl. In some embodiments, $R_{10}$, $R_{11}$ and $R_{12}$ are independently hydrogen, OH or $(C_1$-$C_4)$ alkyl. In other embodiments, $R_{10}$, $R_{11}$ and $R_{12}$ are hydrogen.

In some embodiments, $R_{13}$ is hydrogen or bromine.

In some embodiments, $R_1$ is ($C_1$-$C_4$) alkyl or ($C_1$-$C_4$) perfluoroalkyl and $R_{13}$ is hydrogen or bromine. In other embodiments, $R_1$ is —$CH_3$, —$C_2H_5$, —$C_3H_7$, i-$C_3H_7$, —$CF_3$, —$C_2F_5$, —$C_3F_7$ or i-$C_3F_7$ and $R_{13}$ is hydrogen or bromine In some embodiments, $R_1$ is ($C_1$-$C_4$) alkyl or ($C_1$-$C_4$) perfluoroalkyl and $R_6$ is

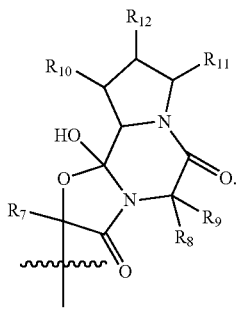

In some of these embodiments, $R_7$ is methyl, ethyl or ispropyl, $R_8$ is hydrogen or methyl, $R_9$ is n-propyl, isopropyl, sec-butyl, isobutyl or benzyl. In some of the above embodiments, $R_{10}$, $R_{11}$ and $R_{12}$ are independently hydrogen, OH or ($C_1$-$C_4$) alkyl. In still other of the above embodiments, $R_{10}$, $R_{11}$ and $R_{12}$ are hydrogen. In still other of the above embodiments, $R_2$ is ($C_1$-$C_2$) alkyl, ($C_1$-$C_2$) substituted alkyl, halo, —$NO_2$, —$OR_{101}$, —$NR_{102}R_{103}$, —$CONR_{104}R_{105}$, —$CO_2R_{106}$ or —$O_2CR_{107}$. In still other of the above embodiments, n is 0 or 1. In still other of the above embodiments, n is 0.1 In still other of the above embodiments, n is 0.

In some embodiments, $R_1$ is —$CH_3$, —$C_2H_5$, —$C_3H_7$, i-$C_3H_7$, —$CF_3$, —$C_2F_5$, —$C_3F_7$ or i-$C_3F_7$ and $R_6$ is

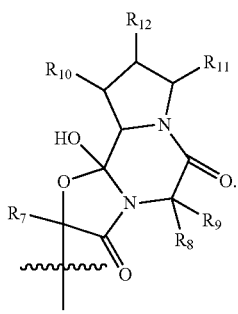

In some of these embodiments, $R_7$ is methyl, ethyl or ispropyl, $R_8$ is hydrogen or methyl, $R_9$ is n-propyl, isopropyl, sec-butyl, isobutyl or benzyl. In some of the above embodiments, $R_{10}$, $R_{11}$ and $R_{12}$ are independently hydrogen, OH or ($C_1$-$C_4$) alkyl. In still other of the above embodiments, $R_{10}$, $R_{11}$ and $R_{12}$ are hydrogen. In still other of the above embodiments, $R_2$ is ($C_1$-$C_2$) alkyl, ($C_1$-$C_2$) substituted alkyl, halo, —$NO_2$, —$OR_{101}$, —$NR_{102}R_{103}$, —$CONR_{104}R_{105}$, —$CO_2R_{106}$ or —$O_2CR_{107}$. In still other of the above embodiments, n is 0 or 1. In still other of the above embodiments, n is 0. In still other of the above embodiments, n is 0.

In some embodiments of a compound of Formula (II): $R_1$ is —$CH_3$, —$C_2H_5$, —$C_3H_7$, i-$C_3H_7$, —$CF_3$, —$C_2F_5$, —$C_3F_7$ or i-$C_3F_7$, $R_2$ is ($C_1$-$C_4$) alkyl, ($C_1$-$C_4$) substituted alkyl, ($C_1$-$C_4$) acyl, ($C_1$-$C_4$) substituted acyl, halo, —$NO_2$, —$OR_{101}$, —$NR_{102}R_{103}$, —$CONR_{104}R_{105}$, —$CO_2R_{106}$ or —$O_2CR_{107}$, n is 0 or 1, $R_5$ is —$CH_3$, —$C_2H_5$, —$C_3H_7$, —$CF_3$, $C_2F_5$ or —$C_3F_7$, $R_6$ is

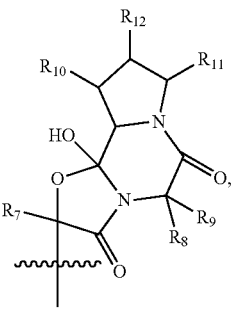

$R_{10}$, $R_{11}$ and $R_{12}$ are independently hydrogen, OH or ($C_1$-$C_4$) alkyl; and $R_{13}$ is hydrogen or bromine In other embodiments of a compound of Formula (I), $R_1$ is $CH_3$, —$C_2H_5$, -n$C_3H_7$, —$CF_3$, $C_2F_5$ or -n$C_3F_7$, $R_2$ is $C_1$-$C_2$) alkyl, ($C_1$-$C_2$) substituted alkyl, halo, —$NO_2$, —$OR_{101}$, —$NR_{102}R_{103}$, —$CONR_{104}R_{105}$, —$CO_2R_{106}$ or —$O_2CR_{107}$; n is 0, $R_5$ is —$CH_3$ or —$CF_3$; $R_6$ is

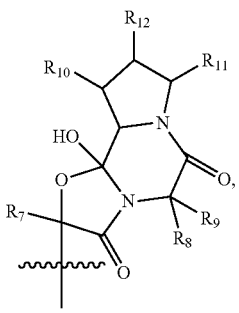

$R_7$ is methyl, ethyl or isopropyl, $R_8$ is hydrogen or methyl, $R_9$ is n-propyl, isopropyl, sec-butyl, isobutyl or benzyl; $R_{10}$, $R_{11}$ and $R_{12}$ are hydrogen; and $R_{13}$ is hydrogen.

Exemplary compound of Formula (I) include the compounds in the table below:

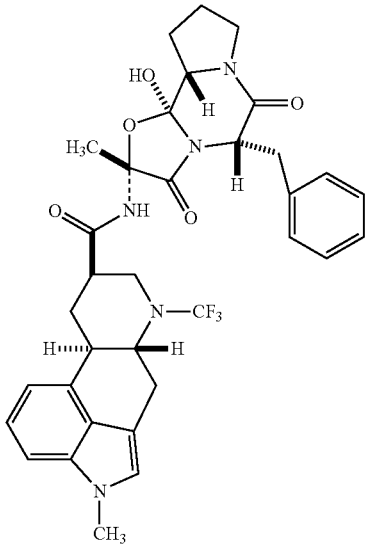

-continued
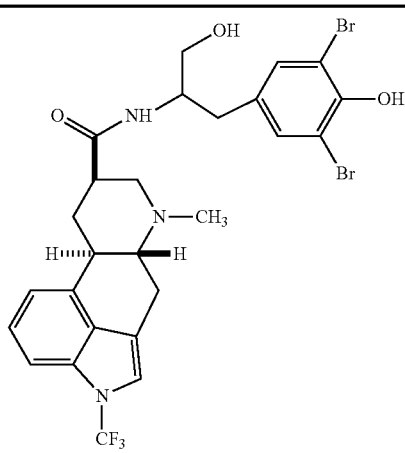
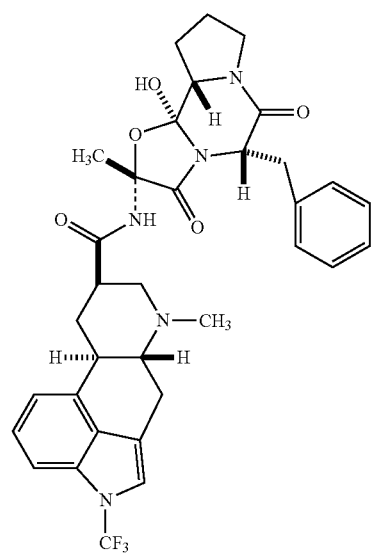
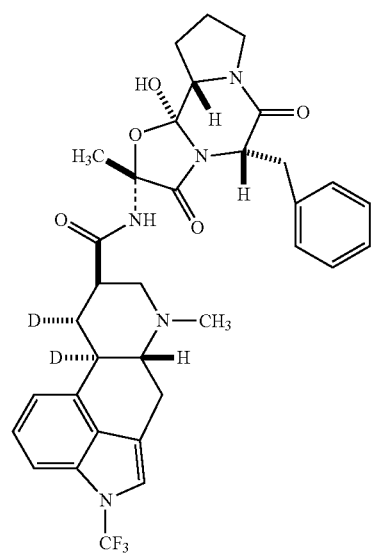
-continued
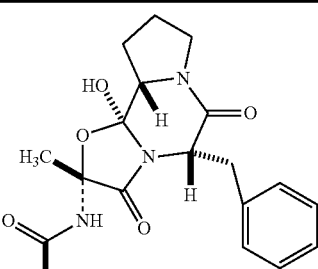
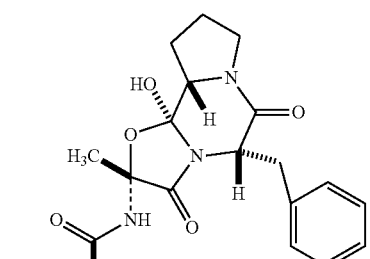
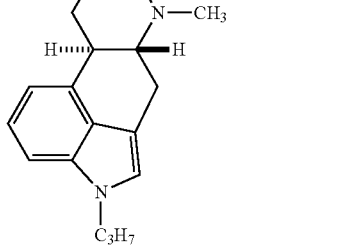
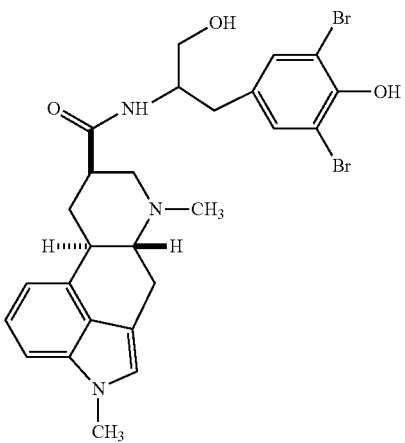

35
-continued
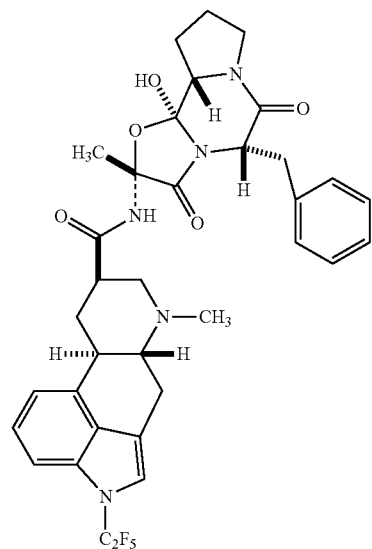
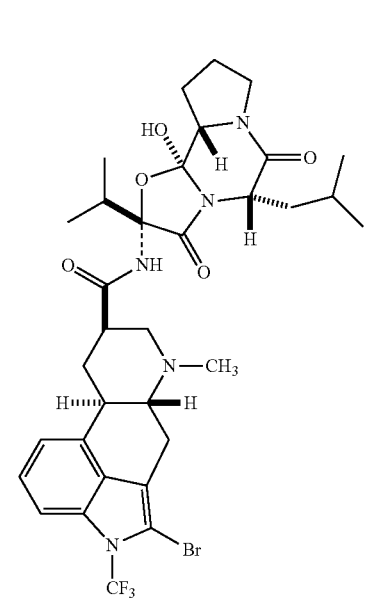
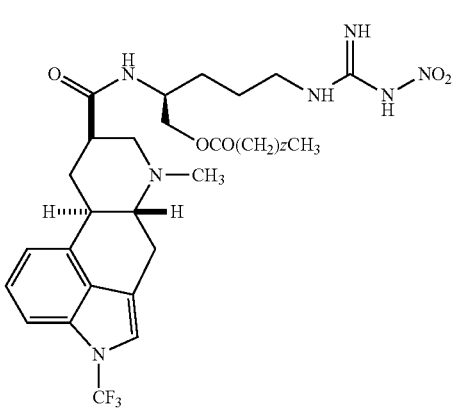
z is 5 or 8
36
-continued
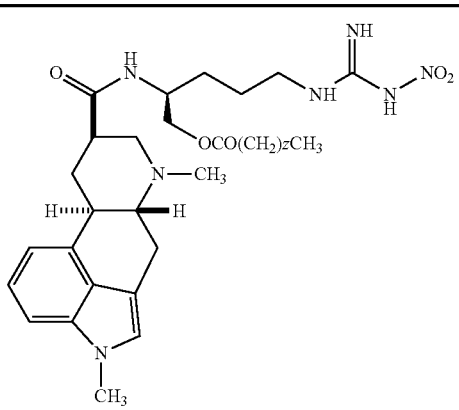
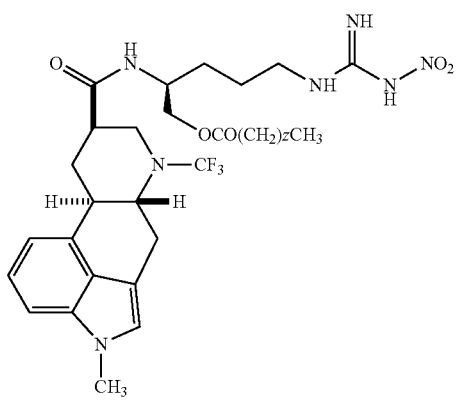
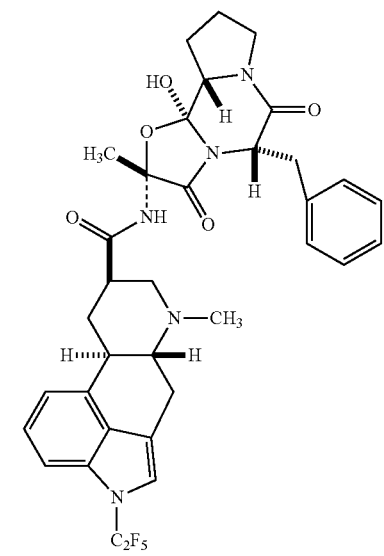

-continued

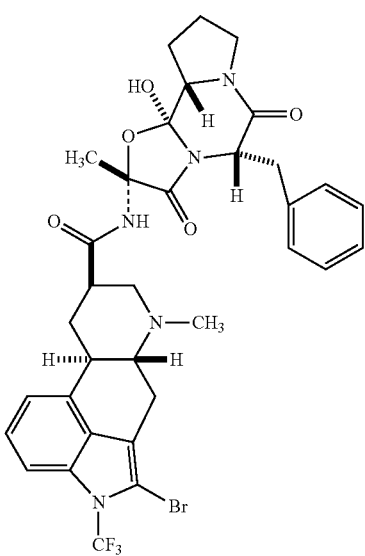

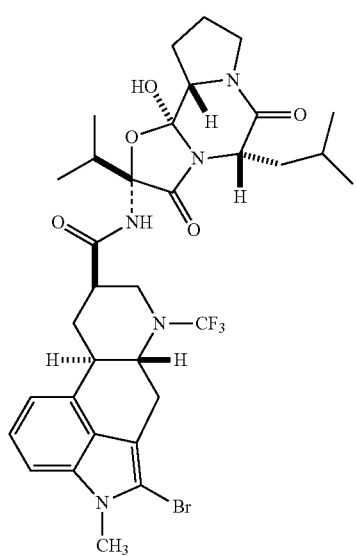

Exemplary compounds of Formula (II) include, for example, the unsaturated analogues of many of the above depicted compounds of Formula (I).

Preparation of the Compounds

Exemplary methods for the preparation of compounds of Formula (I) and (II) for use in the compositions and methods provided herein are described below and in the Examples but other methods known in the art can be used to prepare the ergoline derivatives disclosed herein.

Carboxylic acids (IV) and (V) can be prepared by methods well known to those of skill in the art.

(IV)

(V)

Many methods exist for conversion of carboxylic (IV) and (V) to amides (I) and (II), respectively. Accordingly, preparation of amides (I) and (II) from carboxylic acids (I) and (II) are well within the ambit of the skilled artisan.

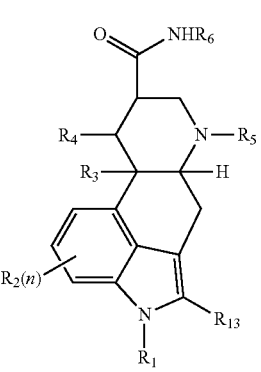

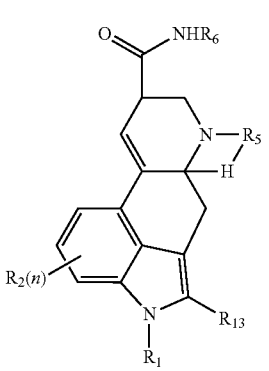

In some embodiments, a method of making a compound of structural formula (III) is provided. The method includes a step of contacting dihydroergotamine with alkaline metal in an organic solvent or a mixture of organic solvents to form a solution and contacting the solution with an alkyl halide selected from the group consisting of benzyl halide, substituted benzyl halide, allyl halide, homallyl halide, substituted allyl halide, methyl halide, ethyl halide, propyl halide, isopropyl halide, butyl halide, isobutyl halide and sec-butyl halide to provide the compound of Formula (III) below.

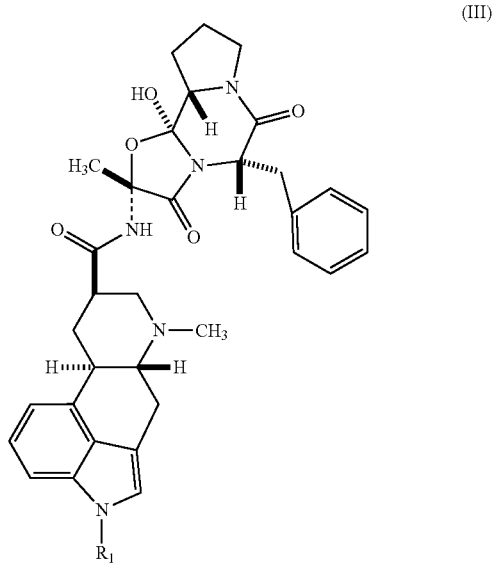

(III)

where $R_1$ is benzyl, substituted benzyl, allyl, substituted allyl, homoallyl, methyl, ethyl, n-propyl, isopropyl, n-butyl, isobutyl or sec-butyl.

In some embodiments, the halide is iodide. In other embodiments, the halide is dissolved in a solvent. In still other embodiments, the solvent is diethyl ether. In still other embodiments, the halide is added dropwise over a period of time.

In some embodiments, the organic solvent or mixture of organic solvents is a mixture of liquid ammonia, absolute ethanol and ether. In other embodiments, the temperature of alkaline metal in the organic solvent or the mixture of organic solvents is between about −78° C. and about −50° C. In still other embodiments, the temperature of alkaline metal in the organic solvent or the mixture of organic solvents is about −78° C. In still other embodiments, the alkaline metal is sodium.

In some embodiments, the ratio of liquid ammonia, ether and absolute ethanol is between about 8:2:1 and about 5:1:1. In other embodiments, the ratio of liquid ammonia, ether and absolute ethanol is about 6.5:1.33:1. In still other embodiments, the molar ratio of alkaline metal to dihydroergotamine is between about 20:1 and about 5:1. In still other embodiments, the molar ratio of alkaline metal to dihydroergotamine is about 10:1. In still other embodiments, the molar ratio of alkyl halide to dihydroergotamine is between about 10:1 and about 2.5:1. In still other embodiments, the molar ratio of alkyl halide to dihydroergotamine is about 5:1.

In some embodiments, the alkyl halide is methyl iodide, the alkaline metal is sodium, the ratio of liquid ammonia, ether and absolute ethanol is about 6.5:1.33:1, the temperature of sodium in liquid ammonia, ether and absolute ethanol is about −78° C., the molar ratio of sodium to dihydroergotamine is about 10:1 and the molar ratio of methyl halide to dihydroergotamine is about 5:1. In other embodiments, methyl iodide is dissolved in diethyl ether and added dropwise over about a 15 minute period.

Pharmaceutical Compositions and Methods of Administration

The pharmaceutical compositions provided herein contain therapeutically effective amounts of one or more of the compounds provided herein that are useful in the prevention, treatment, or amelioration of one or more of the symptoms of diseases or disorders described herein and a pharmaceutically acceptable vehicle. Pharmaceutical vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients.

The compositions contain one or more compounds provided herein. The compounds are, in some embodiments, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as topical administration, transdermal administration and inhaled administration via nebulizers, pressurized metered dose inhalers and dry powder inhalers. In some embodiments, the compounds described above are formulated into pharmaceutical compositions using techniques and procedures well known in the art (see, e.g., Ansel Introduction to Pharmaceutical Dosage Forms, Seventh Edition (1999).

In the compositions, effective concentrations of one or more compounds or pharmaceutically acceptable derivatives thereof is (are) mixed with a suitable pharmaceutical vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the pharmaceutically acceptable vehicle in an amount sufficient to exert a therapeutically useful effect in the absence of undesirable side effects on the patient treated. The therapeutically effective concentration may be determined empirically by testing the compounds in in vitro and in vivo systems well known to those of skill in the art and then extrapolated therefrom for dosages for humans. Human doses are then typically fine-tuned in clinical trials and titrated to response.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In some embodiments, a therapeutically effective dosage should produce a serum concentration of active ingredient of from about 0.001 ng/ml to about 50-200 µg/ml. The pharmaceutical compositions, in other embodiments, should provide a dosage of from about 0.0001 mg to about 70 mg of compound per kilogram of body weight per day. Pharmaceutical dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN®, or dissolution by enhanced ionization (i.e. dissolving in aqueous sodium bicarbonate). Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined The pharmaceutical compositions are provided for administration to humans and animals in unit dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required pharmaceutical vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

In certain embodiments, the compositions are lactose-free compositions containing excipients that are well known in the art and are listed, for example, in the *U.S. Pharmacopeia* (USP) 25-NF20 (2002). In general, lactose-free compositions contains active ingredients, a binder/filler, and a lubricant in pharmaceutically compatible and pharmaceutically acceptable amounts. Particular lactose-free dosage forms contain active ingredients, microcrystalline cellulose, pre-gelatinized starch, and magnesium stearate.

Further provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene laural ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or pharmaceutically acceptable derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (Tween® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of pharmaceutically active compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321: 574 (1989). In other embodiments, polymeric materials can be used. In other embodiments, a controlled release system can be placed in proximity of the therapeutic target, i.e., thus requiring only a fraction of the systemic dose (see, e.g., Goodson, *Medical Applications of Controlled Release*, vol. 2, pp. 115-138 (1984). In some embodiments, a controlled release device is introduced into a subject in proximity of the site of inappropriate immune activation or a tumor. Other controlled release systems are discussed in the review by Langer (*Science* 249:1527-1533 (1990). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbital, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

For nasal administration, the preparation may contain an esterified phosphonate compound dissolved or suspended in a liquid carrier, in particular, an aqueous carrier, for aerosol application. The carrier may contain solubilizing agents such as propylene glycol, surfactants, absorption enhancers such as lecithin or cyclodextrin, or preservatives.

These solutions, particularly those intended for ophthalmic use, may be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same pharmaceutically acceptable substance and by the same methods as for formulations for oral administration.

The compounds provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or pharmaceutically acceptable derivatives may be packaged as articles of manufacture containing packaging material, a compound or pharmaceutically acceptable derivative thereof provided herein, which is effective for treatment, prevention or amelioration of one or more symptoms of the diseases or disorders, supra, within the packaging material, and a label that indicates that the compound or composition, or pharmaceutically acceptable derivative thereof, is used for the treatment, prevention or amelioration of one or more symptoms of the diseases or disorders, supra.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

Dosages

In human therapeutics, the physician will determine the dosage regimen that is most appropriate according to a preventive or curative treatment and according to the age, weight, stage of the disease and other factors specific to the subject to be treated. The pharmaceutical compositions, in other embodiments, should provide a dosage of from about 0.0001 mg to about 70 mg of compound per kilogram of body weight per day. Pharmaceutical dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form. The amount of active ingredient in the formulations provided herein, which will be effective in the prevention or treatment of a disorder or one or more symptoms thereof, will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject.

Exemplary doses of a formulation include milligram or microgram amounts of the active compound per kilogram of subject or sample weight (e.g., from about 1 micrograms per kilogram to about 50 milligrams per kilogram, from about 10 micrograms per kilogram to about 30 milligrams per kilogram, from about 100 micrograms per kilogram to about 10 milligrams per kilogram, or from about 100 microgram per kilogram to about 5 milligrams per kilogram).

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the above described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months.

Methods of Use of the Compounds and Compositions

Methods of treating, preventing, or ameliorating one or more symptoms of diseases including, but not limited to, migraine, ALS, Parkinson's disease, extra-pyramidal disorders, depression, nausea, restless legs syndrome, insomnia, aggression, Huntington's disease, dystonia, parsomnia and hyperlactinemia using the compounds and compositions are provided. In practicing the methods, therapeutically effective amounts of the compounds or compositions, are administered.

Also provided are methods for regulating serotonin transport using the compounds and compositions described herein. In practicing the methods, therapeutically effective amounts of the compounds or compositions, described herein, supra, are administered.

Also provided are methods for antagonizing the 5-HT$_{2B}$, 5-HT$_{2A}$, 5-HT$_7$ and 5-HT$_{2C}$ receptors, D2 and D3 dopamine receptors and A1 and A2 adrenergic receptors using the compounds and compositions, described herein. In practicing the methods, therapeutically effective amounts of the compounds or compositions, described herein, supra, are administered.

Also provided are methods for agonizing the 5-HT$_1$, 5-HT$_{1B}$ and 5-HT$_{1F}$ receptors using the compounds and compositions described herein. In practicing the methods, therapeutically effective amounts of the compounds or compositions, described herein, supra, are administered.

In some embodiments, compounds of Formula (I), infra:

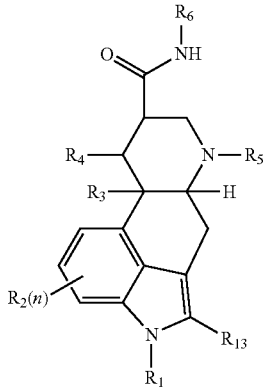

or salts, hydrates or solvates thereof wherein:

$R_1$ is ($C_1$-$C_4$) alkyl, substituted ($C_1$-$C_4$) alkyl or ($C_1$-$C_4$) perfluoroalkyl;

$R_2$ is alkyl, substituted alkyl, acyl, substituted acyl, halo, heteroalkyl, substituted heteroalkyl, —NO$_2$, —N$_3$, —OH, —S(O)$_k$R$_{100}$, —OR$_{101}$, —NR$_{102}$R$_{103}$, —CONR$_{104}$R$_{105}$, —CO$_2$R$_{106}$ or —O$_2$CR$_{107}$;

$R_3$ and $R_4$ are independently hydrogen, deuterium, fluoro, hydroxy or methoxy;

$R_5$ is hydrogen, ($C_1$-$C_3$) alkyl, substituted ($C_1$-$C_4$) alkyl or ($C_1$-$C_3$) perfluoroalkyl;

$R_6$ is

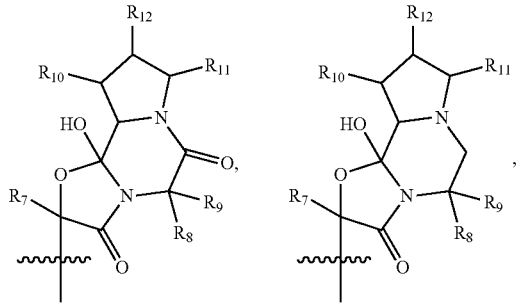

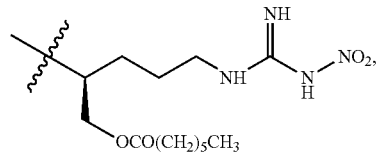

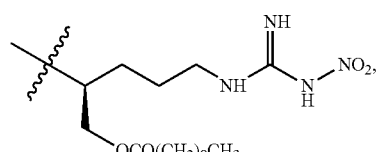

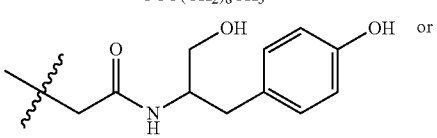

-continued

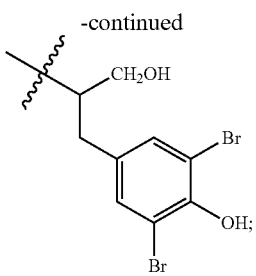

$R_7$ is $(C_1-C_4)$ alkyl;

$R_8$ is hydrogen, $(C_1-C_4)$ alkyl, substituted $(C_1-C_4)$ alkyl, benzyl or substituted benzyl;

$R_9$ is $(C_1-C_4)$ alkyl or benzyl;

$R_{10}$ is hydrogen, OH, =O, $(C_1-C_4)$ alkyl, $(C_1-C_4)$ substituted alkyl, —$CO_2R_{108}$ or —$CONR_{109}R_{110}$;

$R_{11}$ is hydrogen, OH, =O, $(C_1-C_4)$ alkyl, $(C_1-C_4)$ substituted alkyl, —$CO_2R_{111}$ or —$CONR_{112}R_{113}$;

$R_{12}$ is hydrogen, OH, =O, $(C_1-C_4)$ alkyl, $(C_1-C_4)$ substituted alkyl, —$CO_2R_{114}$ or —$CONR_{115}R_{116}$;

$R_{13}$ is hydrogen or halogen;

$R_{101}$-$R_{116}$ are independently hydrogen, alkyl, substituted alkyl, acyl, substituted acyl, aryl, substituted aryl, arylalkyl, substituted arylalkyl, heteroalkyl, substituted hetereoalkyl, heteroaryl, substituted heteroaryl, heteroarylalkyl or substituted heteroarylalkyl; and k is 0, 1 or 2;

n is 0, 1, 2 or 3;

provided that when $R_2$, $R_3$, $R_4$, $R_{10}$, $R_{11}$, $R_{12}$ and $R_{13}$ are hydrogen and $R_6$ is

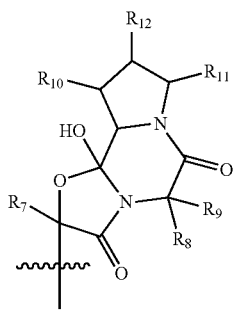

that:

$R_1$ is not allyl;

provided that when $R_1$ and $R_5$ are methyl, $R_2$, $R_3$, $R_4$, $R_{10}$, $R_{11}$, $R_{12}$ and $R_{13}$ are hydrogen and $R_6$ is

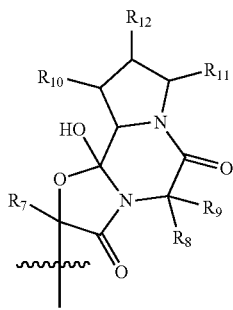

that: $R_7$ is not methyl, $R_8$ is not hydrogen and $R_9$ is not benzyl are used to treat migraine. In other embodiments, compounds of Formula (I), supra, antagonize the 5-HT$_{2B}$, 5-HT$_{2A}$, 5-HT$_7$ and 5-HT$_{2C}$ receptors, D2 and D3 dopamine receptors and A1 and A2 adrenergic receptors. In still other embodiments, compounds of Formula (I), supra, agonize the 5-HT$_1$, 5-HT$_{1B}$ and 5-HT$_{1F}$ receptors.

In other embodiments, compounds of Formula (I), infra:

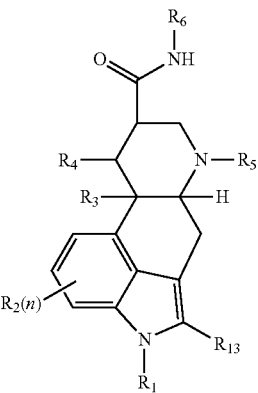

(I)

or salts, hydrates or solvates thereof wherein:

$R_1$ is $(C_1-C_4)$ alkyl substituted $(C_1-C_4)$ alkyl or $(C_1-C_4)$ perfluoroalkyl;

$R_2$ is alkyl, substituted alkyl, acyl, substituted acyl, halo, heteroalkyl, substituted heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$ or —$O_2CR_{107}$;

$R_3$ and $R_4$ are independently hydrogen, deuterium, fluoro, hydroxy or methoxy;

$R_5$ is hydrogen, $(C_1-C_3)$ alkyl or $(C_1-C_3)$ perfluoroalkyl;

$R_6$ is

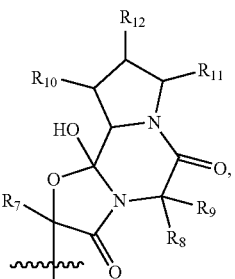 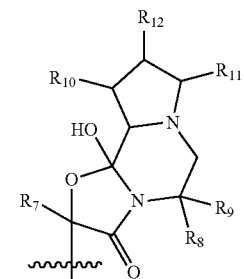

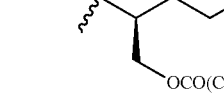

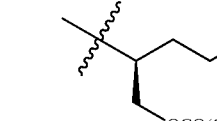

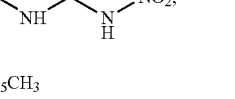

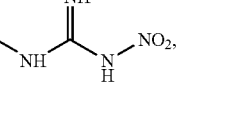

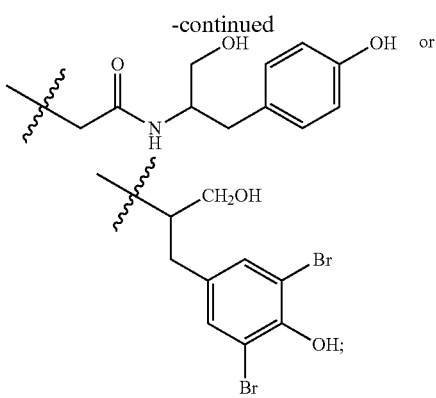

$R_7$ is $(C_1-C_4)$ alkyl;

$R_8$ is hydrogen, $(C_1-C_4)$ alkyl, substituted $(C_1-C_4)$ alkyl, benzyl or substituted benzyl;

$R_9$ is $(C_1-C_4)$ alkyl or benzyl;

$R_{10}$ is hydrogen, OH, =O, $(C_1-C_4)$ alkyl, $(C_1-C_4)$ substituted alkyl, $-CO_2R_{108}$ or $-CONR_{109}R_{110}$;

$R_{11}$ is hydrogen, OH, =O, $(C_1-C_4)$ alkyl, $(C_1-C_4)$ substituted alkyl, $-CO_2R_{111}$ or $-CONR_{112}R_{113}$;

$R_{12}$ is hydrogen, OH, =O, $(C_1-C_4)$ alkyl, $(C_1-C_4)$ substituted alkyl, $-CO_2R_{114}$ or $-CONR_{115}R_{116}$;

$R_{13}$ is hydrogen or halogen;

$R_{101}$-$R_{116}$ are independently hydrogen, alkyl, substituted alkyl, acyl, substituted acyl, aryl, substituted aryl, arylalkyl, substituted arylalkyl, heteroalkyl, substituted hetereoalkyl, heteroaryl, substituted heteroaryl, heteroarylalkyl or substituted heteroarylalkyl; and k is 0, 1 or 2;

n is 0, 1, 2 or 3;

are used to treat or prevent ALS, Parkinson's disease, extra-pyramidal disorders, depression, nausea, restless legs syndrome, insomnia, aggression, Huntington's disease, dystonia, parsomnia and hyperlactinemia. In other embodiments, compounds of Formula (I), supra, antagonize the 5-$HT_{2B}$, 5-$HT_{2A}$, 5-$HT_7$ and 5-$HT_{2C}$ receptors, D2 and D3 dopamine receptors and A1 and A2 adrenergic receptors. In still other embodiments, compounds of Formula (I), supra, agonize the 5-$HT_1$, 5-$HT_{1B}$ and 5-$HT_{1F}$ receptors.

In some embodiments, compounds of Formula (II), infra:

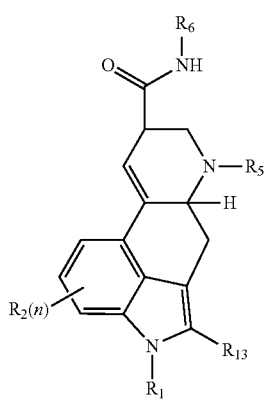

(II)

or salts, hydrates or solvates thereof wherein:

$R_1$ is $(C_1-C_4)$ alkyl, substituted $(C_1-C_4)$ alkyl or $(C_1-C_4)$ perfluoroalkyl;

$R_2$ is alkyl, substituted alkyl, acyl, substituted acyl, halo, heteroalkyl, substituted heteroalkyl, $-NO_2$, $-N_3$, $-OH$, $-S(O)_kR_{100}$, $OR_{101}$, $-NR_{102}R_{103}$, $-CONR_{104}R_{105}$, $-CO_2R_{106}$ or $-O_2CR_{107}$;

$R_5$ is hydrogen, $(C_1-C_3)$ alkyl, substituted $(C_1-C_3)$ alkyl, or $(C_1-C_3)$ perfluoroalkyl;

$R_6$ is

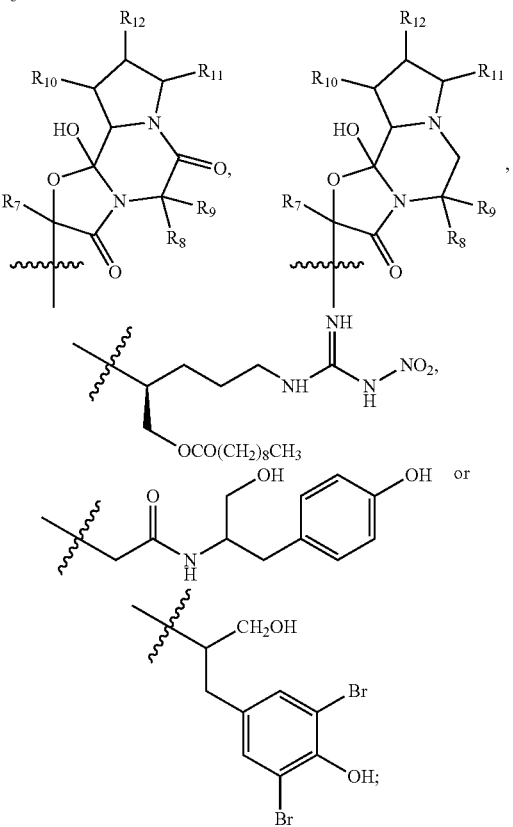

$R_7$ is $(C_1-C_4)$ alkyl;

$R_8$ is hydrogen, $(C_1-C_4)$ alkyl, substituted $(C_1-C_4)$ alkyl, benzyl or substituted benzyl;

$R_9$ is $(C_1-C_4)$ alkyl or benzyl;

$R_{10}$ is hydrogen, OH, =O, $(C_1-C_4)$ alkyl, $(C_1-C_4)$ substituted alkyl, $-CO_2R_{108}$ or $-CONR_{109}R_{110}$;

$R_{11}$ is hydrogen, OH, =O, $(C_1-C_4)$ alkyl, $(C_1-C_4)$ substituted alkyl, $-CO_2R_{111}$ or $-CONR_{112}R_{113}$;

$R_{12}$ is hydrogen, OH, =O, $(C_1-C_4)$ alkyl, $(C_1-C_4)$ substituted alkyl, $-CO_2R_{114}$ or $-CONR_{115}R_{116}$;

$R_{13}$ is hydrogen or halogen;

$R_{101}$-$R_{116}$ are independently hydrogen, alkyl, substituted alkyl, acyl, substituted acyl, aryl, substituted aryl, arylalkyl, substituted arylalkyl, heteroalkyl, substituted hetereoalkyl, heteroaryl, substituted heteroaryl, heteroarylalkyl or substituted heteroarylalkyl; and k is 0, 1 or 2;

n is 0, 1, 2 or 3; are used to treat or prevent ALS, Parkinson's disease, extra-pyramidal disorders, depression, nausea, restless legs syndrome, insomnia, aggression, Huntington's disease, dystonia, parsomnia and hyperlactinemia. In other embodiments, compounds of Formula (II), supra, antagonize the 5-$HT_{2B}$, 5-$HT_{2A}$, 5-$HT_7$ and 5-$HT_{2C}$ receptors, D2 and D3 dopamine receptors and A1 and A2 adrenergic receptors. In still other embodiments, compounds of Formula (II), supra, agonize the 5-$HT_1$, 5-$HT_{1B}$ and 5-$HT_{1F}$ receptors.

Combination Therapy

The compounds and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration of one or more symptoms associated with migraine, ALS, Parkinson's disease, extra-pyramidal disorders, depression, nausea, restless legs syndrome, insomnia, aggression, Huntington's disease, dystonia, parsomnia and hyperlactinemia.

It should be understood that any suitable combination of the compounds and compositions provided herein with one or more of the above therapeutic agents and optionally one or more further pharmacologically active substances are considered to be within the scope of the present disclosure. In some embodiments, the compounds and compositions provided herein are administered prior to or subsequent to the one or more additional active ingredients.

It should also be understood that any suitable combination of the compounds and compositions provided herein may be used with other agents to agonize and or antagonize the receptors mentioned above.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

The following examples are provided for illustrative purposes only and are not intended to limit the scope of the invention.

EXAMPLES

Example 1

Preparation of 1-Methyl-Dihydroergotamine (MAP0057)

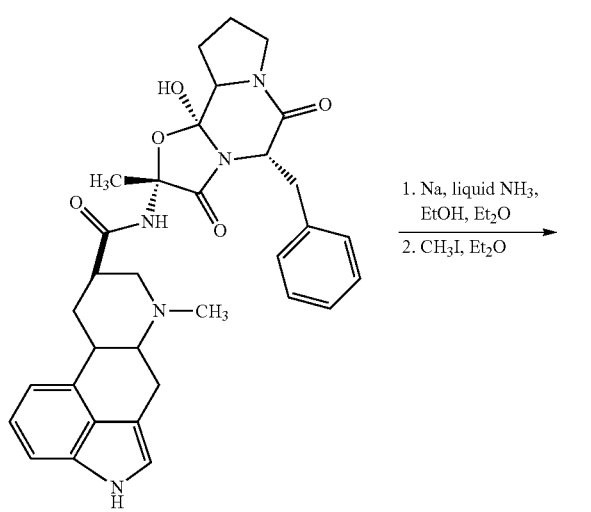

1. Na, liquid NH$_3$, EtOH, Et$_2$O
2. CH$_3$I, Et$_2$O

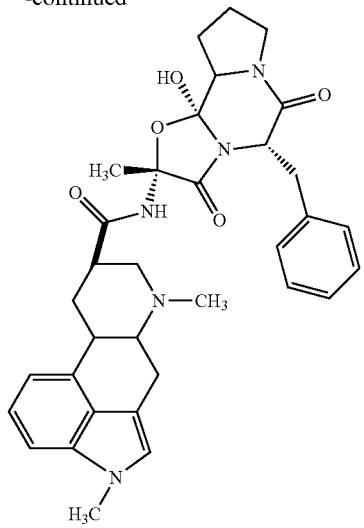

To a solution of sodium metal (2.05 g, 89.1 mmol) in liquid ammonia (200 mL) under N$_2$ at −78° C. was added a solution of absolute ethanol (30 mL) in anhydrous diethyl ether (40 mL) dropwise within 30 min, whereby the initially dark blue solution is decolorized. Dihydroergotamine (5.20 g, 8.90 mmol) was subsequently added to the reaction mixture. The reaction mixture was stirred at −78° C. until the material dissolved completely and a solution of methyl iodide (2.77 mL, 44.5 mmol) in anhydrous diethyl ether (10 mL) was added dropwise within 15 min. After stirring for 30 min at −78° C., the clear solution was carefully heated (maintained the temperature below −30° C.) and the ammonia was evaporated under a partial vacuum. The remaining yellow residue was dissolved in a mixture of methylene chloride (200 mL) and saturated aqueous NaHCO$_3$ (150 mL). The organic phase was washed with an aqueous NaHCO$_3$, brine, dried over Na$_2$SO$_4$, concentrated, and evaporated in vacuo. The residue was purified by column chromatography twice (silica gel, 40 g, 95:5 methylene chloride/MeOH) to afford 1-methyl-dihydroergotamine (3.50 g, 67%) as an off-white solid: mp 216-218° C.; $^1$H NMR (300 MHz, CDCl$_3$) δ 7.42 (d, J=1.4 Hz, 1H), 7.39 (s, 1H), 7.28-7.12 (m, 5H), 6.92 (d, J=7.0 Hz, 1H), 6.74 (d, J=0.9 Hz, 1H), 6.55 (d, J=1.6 Hz, 1H), 6.43 (s, 1H), 4.72 (t, J=6.1 Hz, 1H), 3.76 (s, 3H), 3.70-3.46 (m, 4H), 3.38 (dd, J=14.7, 4.3 Hz, 1H), 3.23 (dd, J=14.0, 6.4 Hz, 1H), 3.13 (d, J=10.4, 2.3 Hz, 1H), 2.97 (t, J=9.2 Hz, 1H), 2.80-2.65 (m, 3H), 2.49 (s, 3H), 2.43 (t, J=11.4 Hz, 1H), 2.29-2.21 (m, 1H), 2.17-1.95 (m, 3H), 1.85-1.62 (m, 2H), 1.57 (s, 3H); HPLC 98.4% (AUC); ESI MS m/z 598 [C$_{34}$H$_{39}$N$_5$O$_5$+H]$^+$.

Example 2

Agonization of the 5-HT$_{2B}$ Receptor with 1-Methyl-Dihydroergotamine

A FLIPR assay was conducted to monitor agonist selectivity for 1-methyl-dihydroergotamine against the 5-HT$_{2B}$ receptor. The assay was completed with an eight point, 4 fold serial dilution series starting with 10 μM concentration to obtain full dose response curve. Percentage activation values were determined for 1-methyl-dihydroergotamine on the 5-HT$_{2B}$ receptor. Agonist selectivity was determined upon initial addition of for 1-methyl-dihydroergotamine followed by a 5 minute incubation at 25° C. Following compound incubation, reference agonists were added at $EC_{80}$. Agonist percentage activation determinations were obtained by assaying 1-methyl-dihydroergotamine and referencing the $E_{max}$ control for the 5-$HT_{2B}$ receptor. The assay was performed by GPCR Profiler™ Service Laboratory, St. Charles, Mo., Millipore, Inc.

The data is summarized in FIG. 1 which illustrates potent agonism of the 5-$HT_{2B}$ receptor for the alpha-Me-5HT experimental control (known potent agonist of $EC_{50}$ of 0.20 nM) and pergolide ($EC_{50}$ of 10 nM) a compound withdrawn from the market due to cardiovascular safety concerns. Ergotamine ($EC_{50}$ of 160 nM) and dihydroergotamine (($EC_{50}$ of 260 nM) are several orders of potency less potent that the control and pergolide, but are still agonists. Importantly, MAP0057 (1-methyl-dihydroergotamine) shows no agonist activity.

Example 3

Competitive Antagonization of the 5-$HT_{2B}$ Receptor with 1-Methyl-Dihydroergotamine A FLIPR assay was conducted to monitor antagonist selectivity for 1-methyl-dihydroergotamine against the 5-$HT_{2B}$ receptor. The assay was completed with an eight point, 4 fold serial dilution series starting with 10 µM concentration to obtain full dose response curve. Percentage inhibition values were determined for 1-methyl-dihydroergotamine on the 5-$HT_{2B}$ receptor. Antagonist percentage inhibition determinations were obtained by assaying 1-methyl-dihydroergotamine and referencing the $E_{max}$ control for the 5-$HT_{2B}$ receptor. The assay above was performed by GPCR Profiler™ Service Laboratory, St. Charles, Mo., Millipore, Inc.

Figure 2:
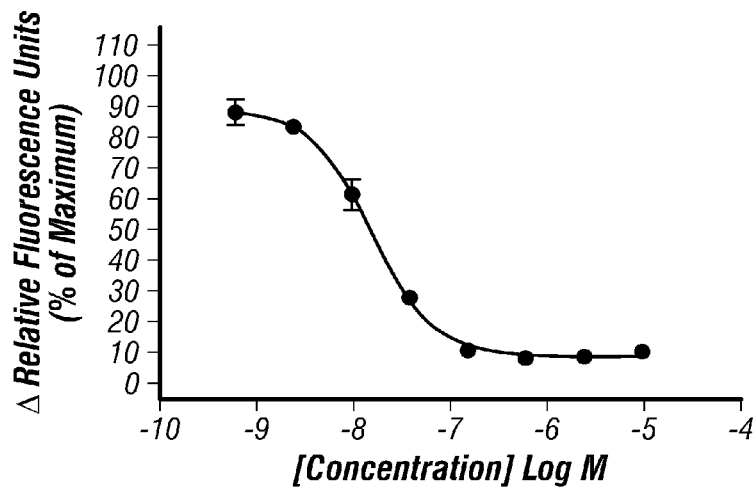
FIG. 2 illustrates the ability of 1-methyl-dihydroergotamine to antagonize the 5-$HT_{2B}$ receptor.

The data is summarized in FIG. 2 which illustrates a reduction in activity with increasing concentrations of 1-methyl-dihydroergotamine showing that MAP0057 (1-methyl-dihydroergotamine) is a potent ($IC_{50}$ of 16 nM) antagonist at the 5-$HT_{2B}$ receptor.

Example 4

Agonization of the 5-$HT_2$, Receptor with 1-Methyl-Dihydroergotamine

The assay was performed analogously to the assay described in Example 2. Pergolide, dihydroergotamine, sumatriptan and MAP0057 (1-methyl-dihydroergotamine) have no agonist activity at the 5-$HT_{2c}$ receptor while alpha-Me-5-HT ($EC_{50}$ of 45 nM) and ergotamine ($EC_{50}$ of 5 µM) have significant agonist activity at the 5-$HT_{2c}$ receptor.

Example 5

Competitive Antagonization of the 5-$HT_{2c}$ Receptor with 1-Methyl-Dihydroergotamine The assay was performed analogously to the assay described in Example 3. Pergolide ($IC_{50}$ of 5 µM), dihydroergotamine ($IC_{50}$ of 280 nM) and MAP0057 (1-methyl-dihydroergotamine, $IC_{50}$ of 460 nM) are significant antagonists of the 5-$HT_{2c}$ receptor while sumatriptan has no antagonist activity at the 5-$HT_{2c}$ receptor.

Example 6

Agonization of the 5-$HT_{1A}$ Receptor with 1-Methyl-Dihydroergotamine

Figure 3:
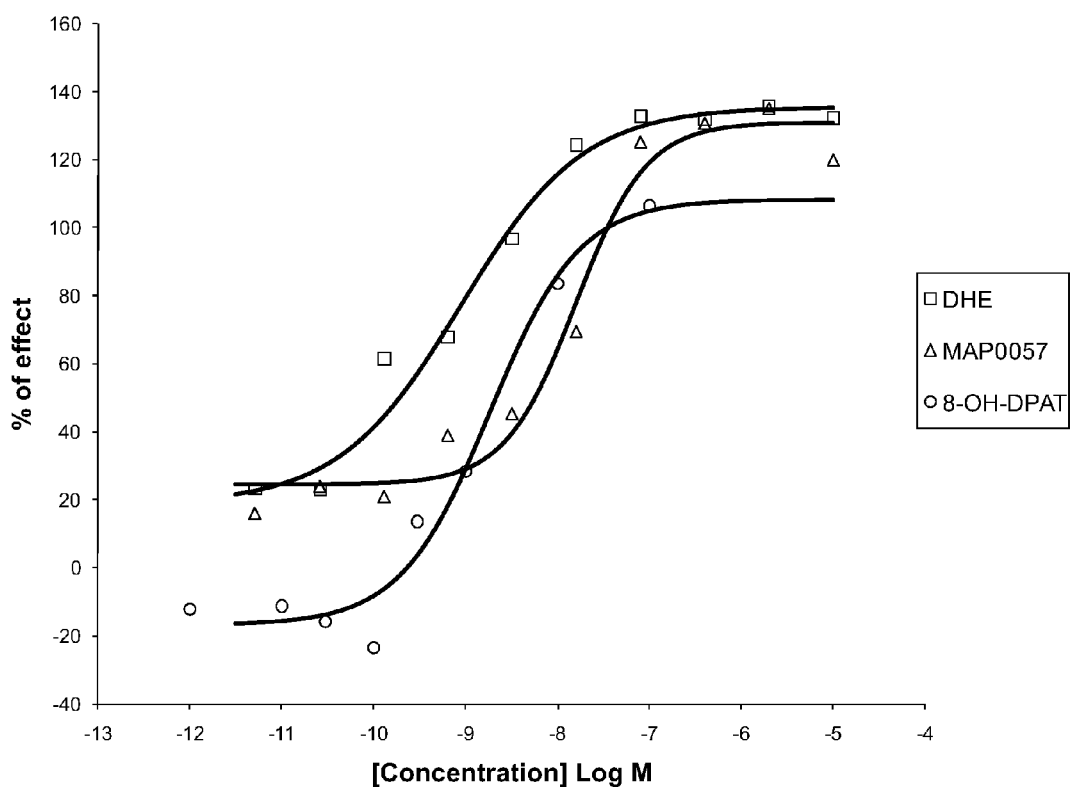
FIG. 3 illustrates the ability of 1-methyl-dihydroergotamine to agonize the 5-$HT_{1A}$ receptor.

A cell based assay (cAMP modulation with HTRF detection) was conducted to monitor agonist activity of test compounds at the 5-$HT_{1A}$ receptor, summarized in FIG. 3. Test compounds were serially diluted to provide a wide concentration range sufficient to calculate $EC_{50}$. The cAMP concentration was determined and results are expressed as a percent of the control response to 100 nM 8-OH-DPAT (control agonist). 1-methyl-dihydroergotamine displayed a strong agonist activity with $EC_{50}$ of 16 nM.

Example 7

Antagonization of the 5-$HT_7$ Receptor with 1-Methyl-Dihydroergotamine

Figure 4:
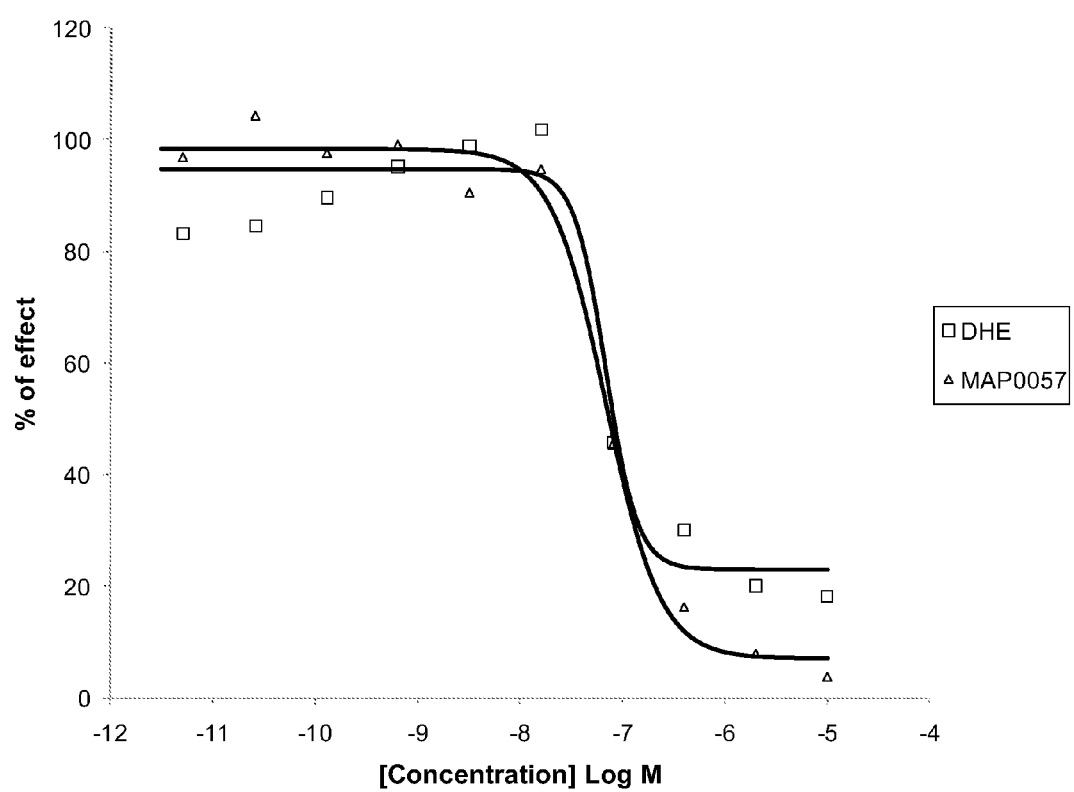
FIG. 4 illustrates the ability of 1-methyl-dihydroergotamine to antagonize the 5-$HT_7$ receptor.

The assay was performed analogously to the assay described in Example 6. Antagonist activity of test compounds at the 5-$HT_7$ receptor, using serotonin as a control reference agonist, was measured. The results are summarized in FIG. 4. Test compounds were serially diluted to provide a wide concentration range sufficient to calculate $IC_{50}$. The results are expressed as a percent of the control response to 300 nM serotonin. 1-methyl-dihydroergotamine displayed a strong antagonist activity with $IC_{50}$ of 69 nm.

Example 8

Agonization of the 5-$HT_{1B}$ Receptor with 1-Methyl-Dihydroergotamine

Figure 5:
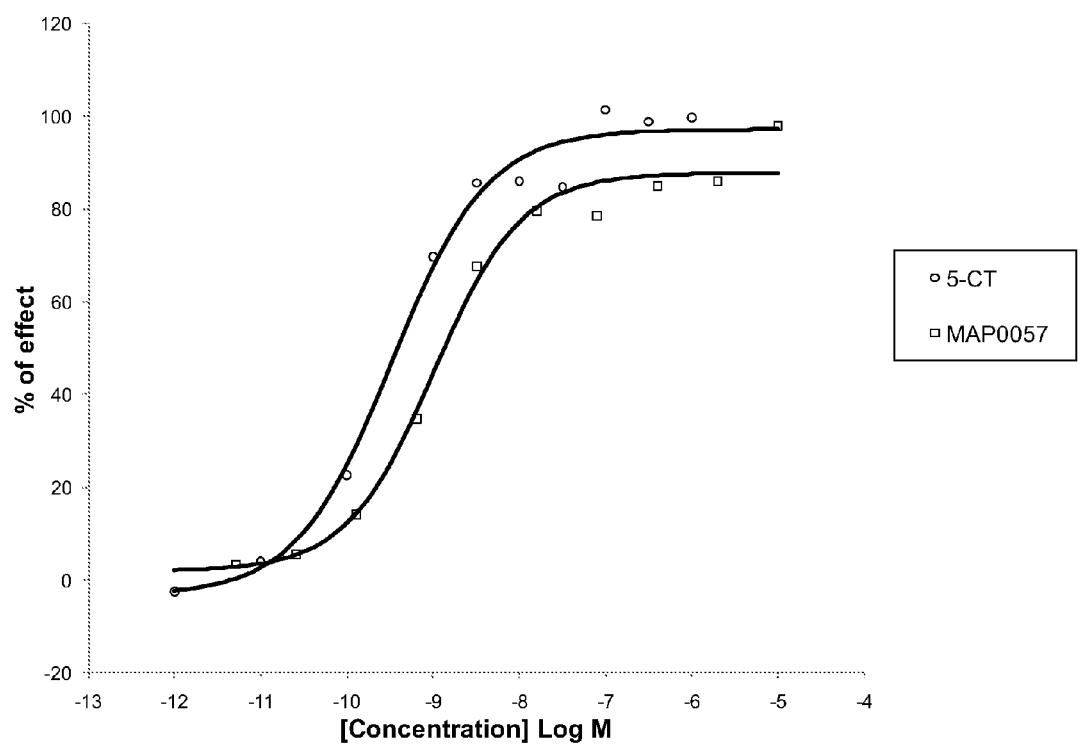
FIG. 5 illustrates the ability of 1-methyl-dihydroergotamine to agonize the 5-$HT_{1B}$ receptor.

A membrane based GTPγS assay was conducted to monitor agonist activity of test compounds at the 5-$HT_{1B}$ receptor, summarized in FIG. 5. Test compounds were serially diluted to provide a wide concentration range sufficient to calculate $EC_{50}$. The results are expressed as a percent of activation. 5-CT was used as a reference agonist. 1-methyl-dihydroergotamine displayed a strong agonist activity with $EC_{50}$ of 1.02 nM.

Example 9

Agonization of the 5-$HT_{1D}$ Receptor with 1-Methyl-Dihydroergotamine

Figure 6:
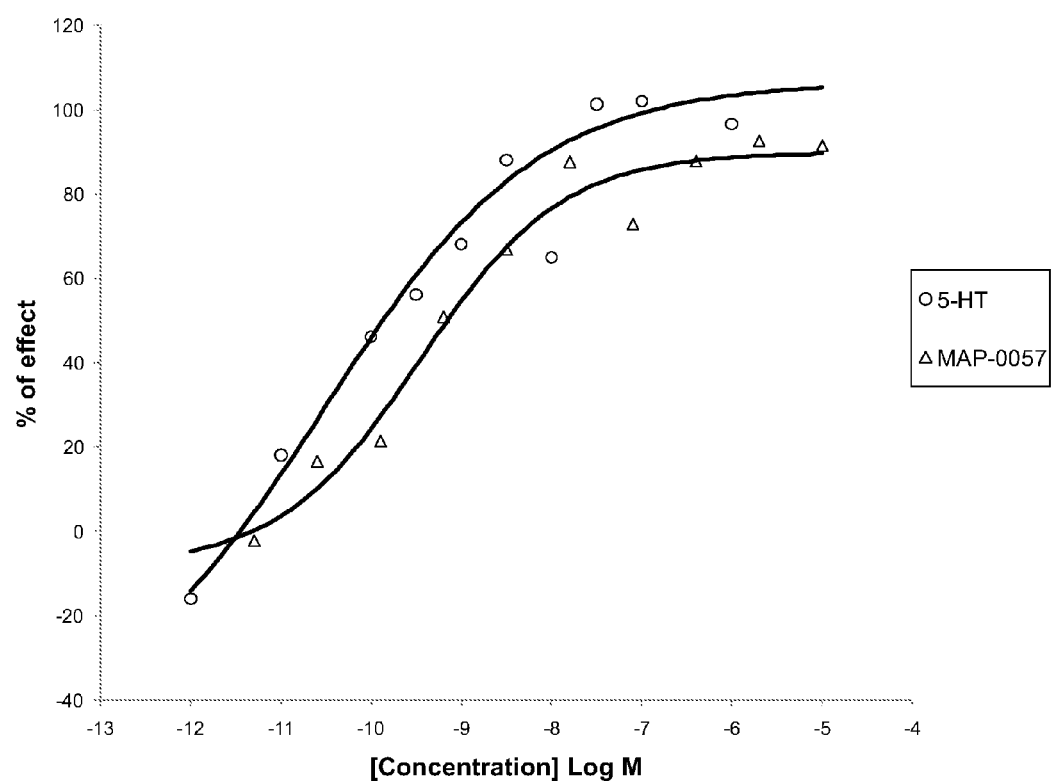
FIG. 6 illustrates the ability of 1-methyl-dihydroergotamine to agonize the 5-$HT_{1D}$ receptor.

The assay was performed analogously to the assay described in Example 10, at the 5-$HT_{1B}$ receptor. The results are summarized in FIG. 6. 5-CT was used as a reference agonist. 1-methyl-dihydroergotamine displayed a strong agonist activity with $EC_{50}$ of 0.45 nM.

What is claimed is:
1. A compound of Formula (I):

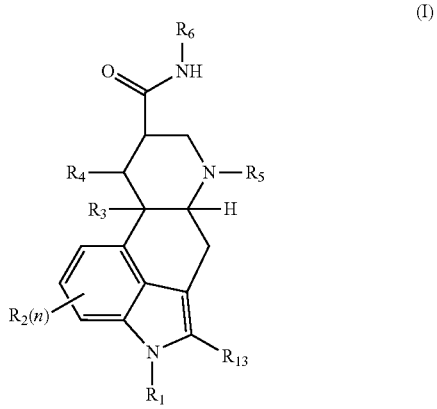

or pharmaceutically acceptable salts, hydrates or solvates thereof wherein:

$R_1$ is $(C_1-C_4)$ alkyl, substituted $(C_1-C_4)$ alkyl or $(C_1-C_4)$ perfluoroalkyl;

$R_2$ is alkyl, substituted alkyl, acyl, substituted acyl, halo, heteroalkyl, substituted heteroalkyl, —$NO_2$, —$N_3$, —OH, —$S(O)_kR_{100}$, —$OR_{101}$, —$NR_{102}R_{103}$, —$CONR_{104}R_{105}$, —$CO_2R_{106}$ or —$OC(O)R_{107}$;

$R_3$ and $R_4$ are independently hydrogen, deuterium, fluoro, hydroxy or methoxy;

$R_5$ is hydrogen, $(C_1-C_3)$ alkyl, substituted $(C_1-C_4)$ alkyl or $(C_1-C_3)$ perfluoroalkyl;

$R_6$ is

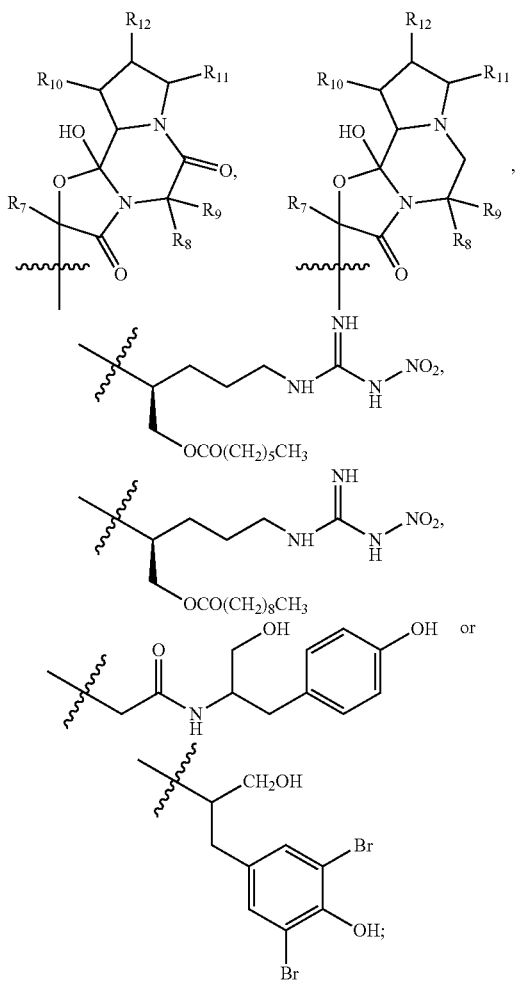

$R_7$ is sec-butyl, isobutyl, t-butyl, benzyl, $(C_2-C_4)$ alkenyl or $(C_2-C_4)$ alkynyl;

$R_8$ is hydrogen, $(C_1-C_4)$ alkyl, substituted $(C_1-C_4)$ alkyl, benzyl or substituted benzyl;

$R_9$ is methyl, ethyl, propyl, isopropyl, n-butyl, isobutyl, t-butyl, benzyl, $(C_2-C_4)$ alkenyl or $(C_2-C_4)$ alkynyl;

$R_{10}$ is hydrogen, OH, =O, $(C_1-C_4)$ alkyl, $(C_1-C_4)$ substituted alkyl, —$CO_2R_{108}$ or —$CONR_{109}R_{110}$;

$R_{11}$ is hydrogen, OH, =O, $(C_1-C_4)$ alkyl, $(C_1-C_4)$ substituted alkyl, —$CO_2R_{111}$ or —$CONR_{112}R_{113}$;

$R_{12}$ is hydrogen, OH, =O, $(C_1-C_4)$ alkyl, $(C_1-C_4)$ substituted alkyl, —$CO_2R_{114}$ or —$CONR_{115}R_{116}$;

$R_{13}$ is hydrogen or halogen;

$R_{101}$, $R_{102}$, $R_{103}$, $R_{104}$, $R_{105}$, $R_{106}$, $R_{107}$, $R_{108}$, $R_{109}$, $R_{110}$, $R_{111}$, $R_{112}$, $R_{113}$, $R_{114}$, $R_{115}$ and $R_{116}$ are independently hydrogen, alkyl, substituted alkyl, acyl, substituted acyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; and k is 0, 1 or 2;

n is 0, 1, 2 or 3;

wherein substituted with reference to a saturated carbon atom is limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —$NO_2$, =$N_2$, —$N_3$, —$S(O)_2R^b$, —$S(O)_2NR^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S; and substituted with reference to an unsaturated carbon atom or an nitrogen atom in a heteroalkyl group is limited to —$R^a$, halo, —$O^-$, —$OR^b$, —$SR^b$, —$S^-$, —$NR^cR^c$, trihalomethyl, —$CF_3$, —CN, —OCN, —SCN, —NO, —$NO_2$, —$N_3$, —$S(O)_2R^b$, —$S(O)_2O^-$, —$S(O)_2OR^b$, —$OS(O)_2R^b$, —$OS(O)_2O^-$, —$OS(O)_2OR^b$, —$P(O)(O^-)_2$, —$P(O)(OR^b)(O^-)$, —$P(O)(OR^b)(OR^b)$, —$C(O)R^b$, —$C(S)R^b$, —$C(NR^b)R^b$, —$C(O)O^-$, —$C(O)OR^b$, —$C(S)OR^b$, —$C(O)NR^cR^c$, —$C(NR^b)NR^cR^c$, —$OC(O)R^b$, —$OC(S)R^b$, —$OC(O)O^-$, —$OC(O)OR^b$, —$OC(S)OR^b$, —$NR^bC(O)R^b$, —$NR^bC(S)R^b$, —$NR^bC(O)O^-$, —$NR^bC(O)OR^b$, —$NR^bC(S)OR^b$, —$NR^bC(O)NR^cR^c$, —$NR^bC(NR^b)R^b$ and —$NR^bC(NR^b)NR^cR^c$ where $R^a$, $R^b$ and $R^c$ are as defined above;

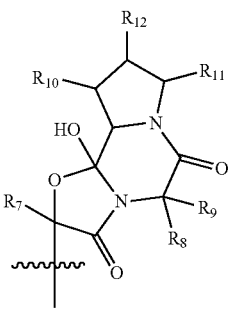

provided that when $R_2$, $R_3$, $R_4$, $R_{10}$, $R_{11}$, $R_{12}$ and $R_{13}$ are hydrogen and $R_6$ is O that:

$R_1$ is not allyl;

provided that when $R_1$ is $(C_1-C_4)$ alkyl and $R_2$, $R_3$, $R_4$, $R_{10}$, $R_{11}$, $R_{12}$ and $R_{13}$ are hydrogen that:

$R_6$ is not

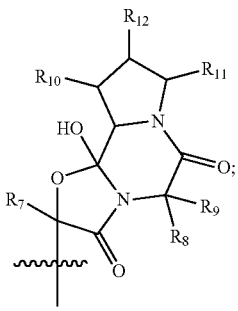

provided that when $R_1$ and $R_5$ are methyl and $R_2$, $R_3$ and $R_4$ are hydrogen that: $R_6$ is not

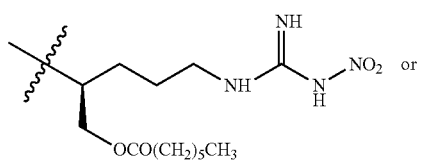

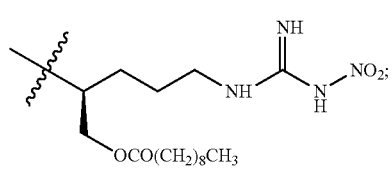

provided that when $R_1$ and $R_5$ are methyl and $R_2$, $R_3$ and $R_4$ are hydrogen that: $R_6$ is not

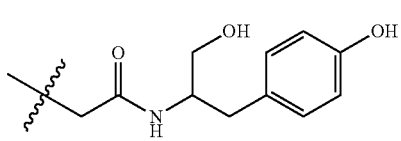 [SMILES: *CC(=O)NC(CO)Cc1ccc(O)cc1]

provided that when $R_1$ and $R_5$ are methyl and $R_2$, $R_3$ and $R_4$ are hydrogen that: $R_6$ is not

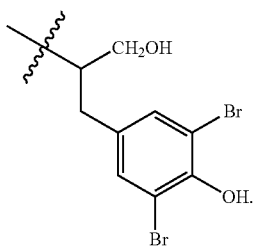 [SMILES: *C(CO)Cc1cc(Br)c(O)c(Br)c1]

2. The compound of claim 1, wherein $R_1$ is $(C_1-C_4)$ alkyl or $(C_1-C_4)$ perfluoroalkyl and $R_6$ is

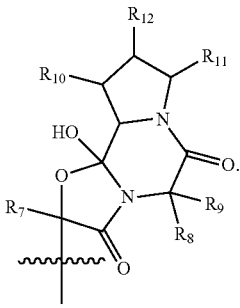

3. The compound of claim 1, wherein $R_1$ is —CH$_3$, —C$_2$H$_5$, —C$_3$H$_7$, i-C$_3$H$_7$, —CF$_3$, —C$_2$F$_5$, —C$_3$F$_7$ or i-C$_3$F$_7$ and $R_6$ is

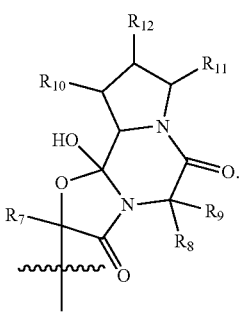

4. The compound of claim 1, wherein $R_1$ is —CH$_3$, —C$_2$H$_5$, —C$_3$H$_7$, i-C$_3$H$_7$, —CF$_3$, —C$_2$F$_5$, —C$_3$F$_7$ or i-C$_3$F$_7$, $R_2$ is $(C_1-C_4)$ alkyl, $(C_1-C_4)$ substituted alkyl, $(C_1-C_4)$ acyl, $(C_1-C_4)$ substituted acyl, halo, —NO$_2$, —OR$_{101}$, —NR$_{102}$R$_{103}$, —CONR$_{104}$R$_{105}$, —CO$_2$R$_{106}$ or —OC(O)R$_{107}$, n is 0 or 1, $R_3$ and $R_4$ are independently hydrogen or deuterium, $R_5$ is —CH$_3$, —C$_2$H$_5$, —C$_3$H$_7$, —CF$_3$, C$_2$F$_5$ or —C$_3$F$_7$, $R_6$ is

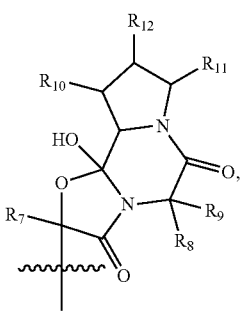

$R_{10}$, $R_{11}$ and $R_{12}$ are independently hydrogen, OH or $(C_1-C_4)$ alkyl; and $R_{13}$ is hydrogen or bromine.

5. The compound of claim 1 having the structure:

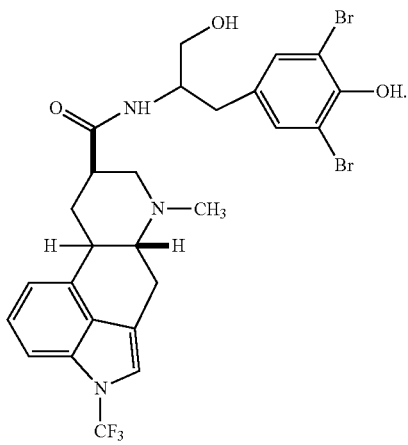 [SMILES: CN1C[C@H](C(=O)NC(CO)Cc2cc(Br)c(O)c(Br)c2)CC2c3cccc4c3c(cn4C(F)(F)F)C[C@H]21]

6. The compound of claim 1 having the structure:

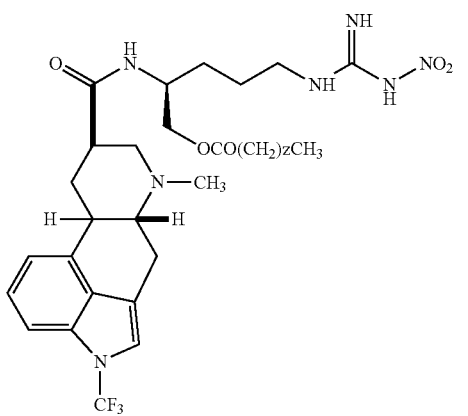

wherein z is 5 or 8.

7. A pharmaceutical composition comprising the compound of claim 1 and a pharmaceutically acceptable vehicle.

8. A compound of Formula (II):

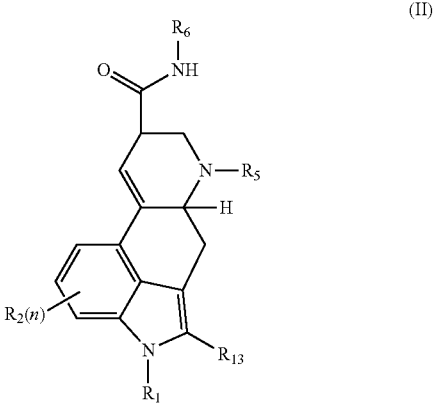

or pharmaceutically acceptable salts, hydrates or solvates thereof wherein:

$R_1$ is $(C_1\text{-}C_4)$ alkyl, substituted $(C_1\text{-}C_4)$ alkyl or $(C_1\text{-}C_4)$ perfluoroalkyl;

$R_2$ is alkyl, substituted alkyl, acyl, substituted acyl, halo, heteroalkyl, substituted heteroalkyl, $-NO_2$, $-N_3$, $-OH$, $-S(O)_kR_{100}$, $-OR_{101}$, $-NR_{102}R_{103}$, $-CONR_{104}R_{105}$, $-CO_2R_{106}$ or $-OC(O)R_{107}$;

$R_5$ is hydrogen, $(C_1\text{-}C_3)$ alkyl, substituted $(C_1\text{-}C_3)$ alkyl, or $(C_1\text{-}C_3)$ perfluoroalkyl;

$R_6$ is

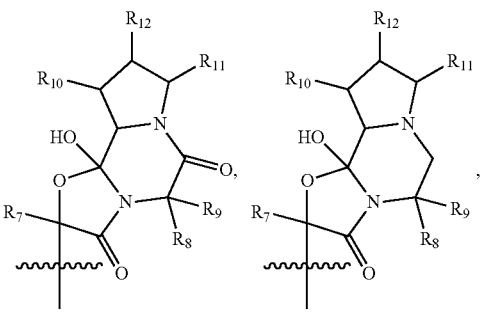

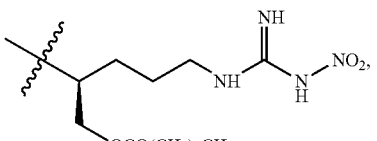

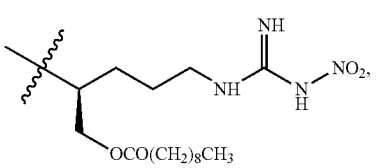

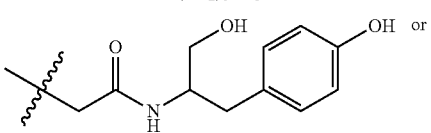

-continued

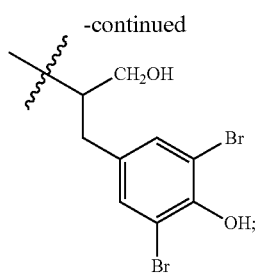

$R_7$ is $(C_1-C_4)$ alkyl;
$R_8$ is hydrogen, ethyl, propyl, isopropyl, n-butyl, sec-butyl, isobutyl, t-butyl, substituted $(C_1-C_4)$ alkyl, $(C_2-C_4)$ alkenyl or $(C_2-C_4)$ alkynyl, benzyl or substituted benzyl;
$R_9$ is methyl, ethyl, propyl, isopropyl, n-butyl, sec-butyl, t-butyl, $(C_2-C_4)$ alkenyl or $(C_2-C_4)$ alkynyl;
$R_{10}$ is hydrogen, OH, =O, $(C_1-C_4)$ alkyl, $(C_1-C_4)$ substituted alkyl, $-CO_2R_{108}$ or $-CONR_{109}R_{110}$;
$R_{11}$ is hydrogen, OH, =O, $(C_1-C_4)$ alkyl, $(C_1-C_4)$ substituted alkyl, $-CO_2R_{111}$ or $-CONR_{112}R_{113}$;
$R_{12}$ is hydrogen, OH, =O, $(C_1-C_4)$ alkyl, $(C_1-C_4)$ substituted alkyl, $-CO_2R_{114}$ or $-CONR_{115}R_{116}$;
$R_{13}$ is hydrogen or halogen;
$R_{101}, R_{102}, R_{103}, R_{104}, R_{105}, R_{106}, R_{107}, R_{108}, R_{109}, R_{110}, R_{111}, R_{112}, R_{113}, R_{114}, R_{115}$ and $R_{116}$ are independently hydrogen, alkyl, substituted alkyl, acyl, substituted acyl, aryl, substituted aryl, arylalkyl, substituted arylalkyl, heteroalkyl, substituted heteroalkyl, heteroaryl, substituted heteroaryl, heteroarylalkyl or substituted heteroarylalkyl; and
k is 0, 1 or 2;
n is 0, 1, 2 or 3;
wherein substituted with reference to a saturated carbon atom is limited to $-R^a$, halo, $-O^-$, =O, $-OR^b$, $-SR^b$, $-S^-$, =S, $-NR^cR^c$, =$NR^b$, =$N-OR^b$, trihalomethyl, $-CF_3$, $-CN$, $-OCN$, $-SCN$, $-NO$, $-NO_2$, =$N_2$, $-N_3$, $-S(O)_2R^b$, $-S(O)_2NR^b$, $-S(O)_2O^-$, $-S(O)_2OR^b$, $-OS(O)_2R^b$, $-OS(O)_2O^-$, $-OS(O)_2 OR^b$, $-P(O)(O^-)_2$, $-P(O)(OR^b)(O^-)$, $-P(O)(OR^b)(OR^b)$, $-C(O)R^b$, $-C(S)R^b$, $-C(NR^b)R^b$, $-C(O)O^-$, $-C(O)OR^b$, $-C(S)OR^b$, $-C(O)NR^cR^c$, $-C(NR^b)NR^cR^c$, $-OC(O)R^b$, $-OC(S)R^b$, $-OC(O)O^-$, $-OC(O)OR^b$, $-OC(S)OR^b$, $-NR^bC(O)R^b$, $-NR^bC(S)R^b$, $-NR^bC(O)O^-$, $-NR^bC(O)OR^b$, $-NR^bC(S)OR^b$, $-NR^bC(O)NR^cR^c$, $-NR^bC(NR^b)R^b$ and $-NR^bC(NR^b)NR^cR^c$, where $R^a$ is selected from the group consisting of alkyl, cycloalkyl, heteroalkyl, cycloheteroalkyl, aryl, arylalkyl, heteroaryl and heteroarylalkyl; each $R^b$ is independently hydrogen or $R^a$; and each $R^c$ is independently $R^b$ or alternatively, the two $R^c$s are taken together with the nitrogen atom to which they are bonded form a 4-, 5-, 6- or 7-membered cycloheteroalkyl which may optionally include from 1 to 4 of the same or different additional heteroatoms selected from the group consisting of O, N and S; and substituted with reference to an unsaturated carbon atom or an nitrogen atom in a heteroalkyl group is limited to $-R^a$, halo, $-O^-$, $-OR^b$, $-SR^b$, $-S^-$, $-NR^cR^c$, trihalomethyl, $-CF_3$, $-CN$, $-OCN$, $-SCN$, $-NO$, $-NO_2$, $-N_3$, $-S(O)_2R^b$, $-S(O)_2O^-$, $-S(O)_2OR^b$, $-OS(O)_2R^b$, $-OS(O)_2O^-$, $-OS(O)_2OR^b$, $-P(O)(O^-)_2$, $-P(O)(OR^b)(O^-)$, $-P(O)(OR^b)(OR^b)$, $-C(O)R^b$, $-C(S)R^b$, $-C(O)NR^cR^c$, $-C(NR^b)NR^cR^c$, $-OC(O)R^b$, $-OC(S)R^b$, $-OC(O)O^-$, $-OC(O)OR^b$, $-OC(S)OR^b$, $-NR^bC(O)R^b$, $-NR^bC(S)R^b$, $-NR^bC(O)O^-$, $-NR^bC(O)OR^b$, $-NR^bC(S)OR^b$, $-NR^bC(O)NR^cR^c$, $-NR^bC(NR^b)R^b$ and $-NR^bC(NR^b)NR^cR^c$ where $R^a$, $R^b$ and $R^c$ are as defined above;
provided that when $R_1$ and $R_5$ are methyl, $R_2, R_{10}, R_{11}, R_{12}$ and $R_{13}$ are hydrogen and $R_6$ is

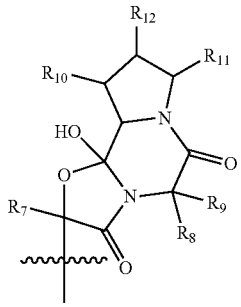

that:
$R_7$ is not methyl, $R_8$ is not hydrogen and $R_9$ is not benzyl;
$R_7$ is not methyl, $R_8$ is not hydrogen and $R_9$ is not sec-butyl;
$R_7$ is not ethyl, $R_8$ is not hydrogen and $R_9$ is not isopropyl;
$R_7$ is not isopropyl, $R_8$ is not hydrogen and $R_9$ is not isopropyl;
provided that when $R_1$ is $CH_2OH$, $R_5$ is methyl, $R_2, R_{10}, R_{11}$, and $R_{12}$ are hydrogen, $R_{13}$ is bromine and $R_6$ is

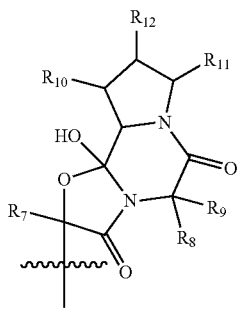

that:
$R_7$ is not isopropyl, $R_8$ is not hydrogen and $R_9$ is not sec-butyl.

9. The compound of claim 8, wherein $R_6$ is

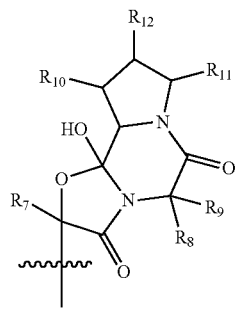

$R_7$ is methyl, ethyl or isopropyl, $R_8$ is hydrogen, $R_9$ is n-propyl, isopropyl or sec-butyl and $R_{10}, R_{11}$ and $R_{12}$ are hydrogen.

10. The compound of claim 8, wherein $R_1$ is $(C_1-C_4)$ alkyl or $(C_1-C_4)$ perfluoroalkyl and $R_6$ is

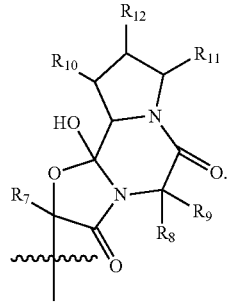

11. The compound of claim 8, wherein $R_1$ is —$CH_3$, —$C_2H_5$, —$C_3H_7$, i-$C_3H_7$, —$CF_3$, —$C_2F_5$, —$C_3F_7$ or i-$C_3F_7$ and $R_6$ is

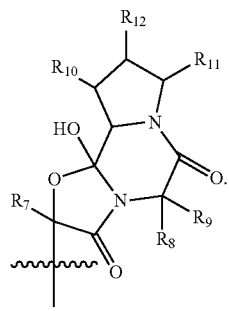

12. The compound of claim 8, wherein $R_1$ is —$CH_3$, —$C_2H_5$, —$C_3H_7$, i-$C_3H_7$, —$CF_3$, —$C_2F_5$, —$C_3F_7$ or i-$C_3F_7$, $R_2$ is $(C_1-C_4)$ alkyl, $(C_1-C_4)$ substituted alkyl, $(C_1-C_4)$ acyl, $(C_1-C_4)$ substituted acyl, halo, —$NO_2$, —$OR_{101}$, —$NR_{102}R_{103}$, —$CONR_{104}R_{105}$, —$CO_2R_{106}$ or —$OC(O)R_{107}$, n is 0 or 1, $R_5$ is —$CH_3$, —$C_2H_5$, —$C_3H_7$, —$CF_3$, $C_2F_5$ or —$C_3F_7$, $R_6$ is

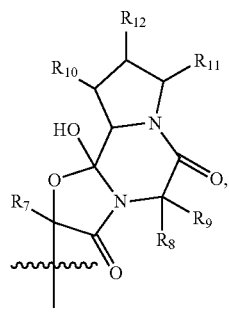

$R_{10}$, $R_{11}$ and $R_{12}$ are independently hydrogen, OH or $(C_1-C_4)$ alkyl; and $R_{13}$ is hydrogen or bromine.

13. The compound of claim 8, wherein $R_1$ is —$CH_3$, —$C_2H_5$, -n-$C_3H_7$, —$CF_3$, —$C_2F_5$ or -n-$C_3F_7$, $R_2$ is $(C_1-C_2)$ alkyl, $(C_1-C_2)$ substituted alkyl, halo, —$NO_2$, —$OR_{101}$, —$NR_{102}R_{103}$, —$CONR_{104}R_{105}$, —$CO_2R_{106}$ or —$OC(O)R_{107}$, n is 0, $R_5$ is —$CH_3$ or —$CF_3$, $R_6$ is

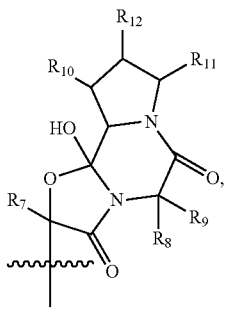

$R_7$ is methyl, ethyl or isopropyl, $R_8$ is hydrogen, $R_9$ is n-propyl, isopropyl, sec-butyl, or benzyl, $R_{10}$, $R_{11}$ and $R_{12}$ are hydrogen; and $R_{13}$ is hydrogen.

14. The compound of claim 8, having the structure:

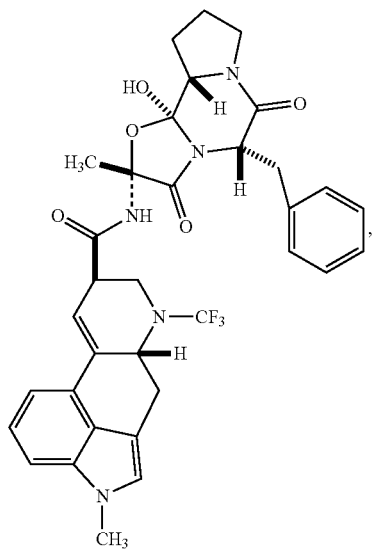

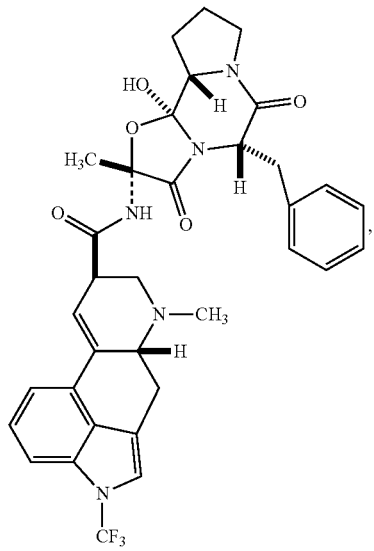

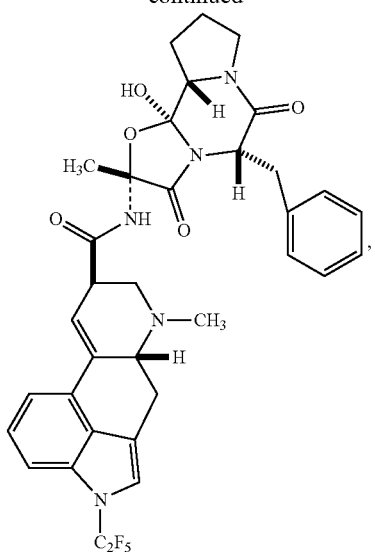
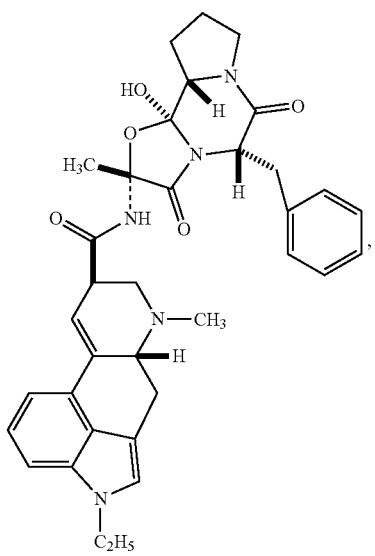
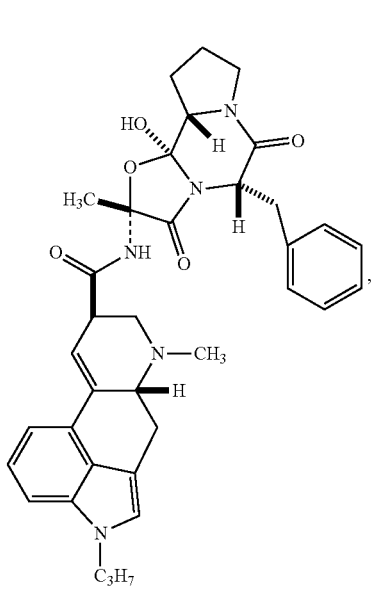
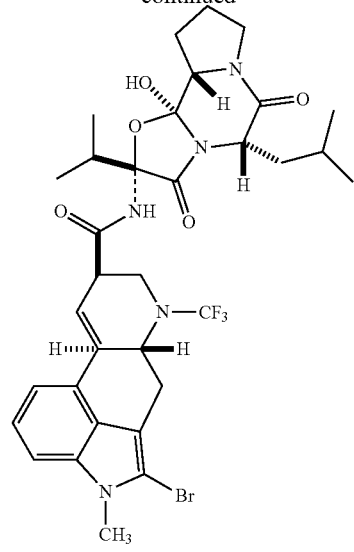
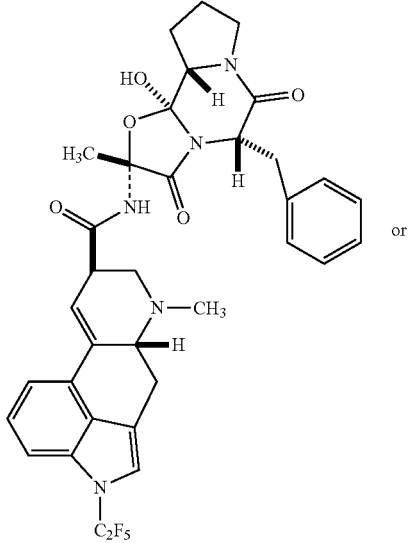
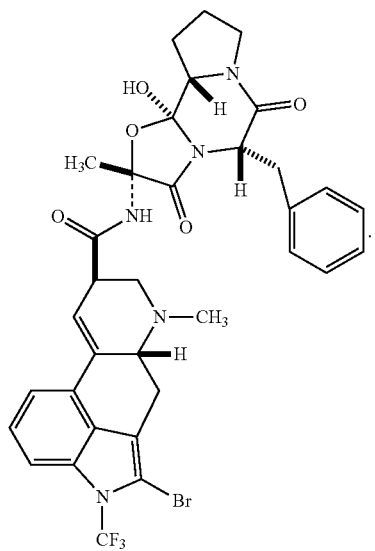

15. The compound of claim 8, having structure:
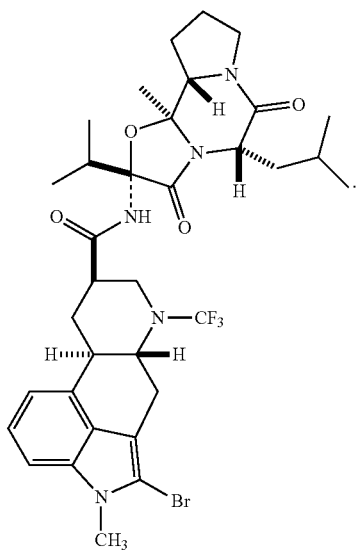
16. The compound of claim 8 having the structure:
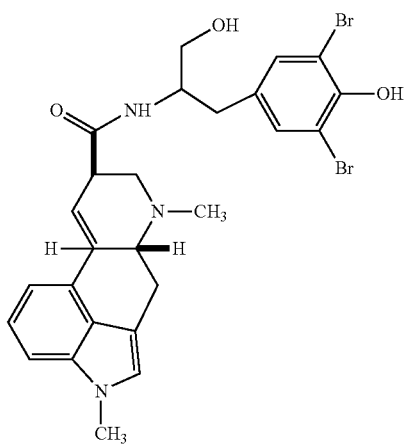
or
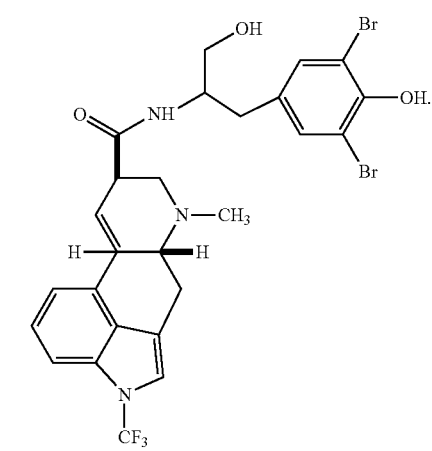
17. The compound of claim 8, having the structure:
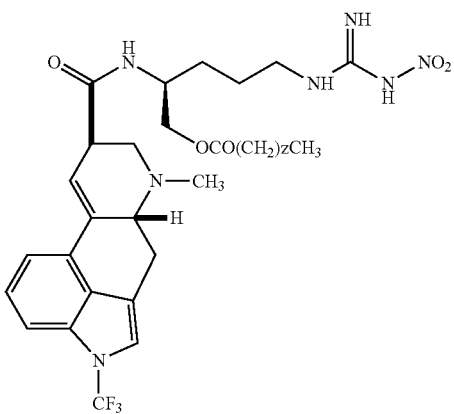
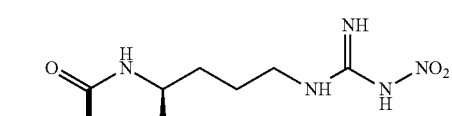
or
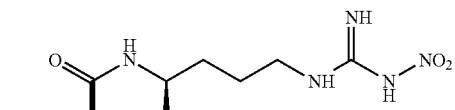
wherein z is 5 or 8.
18. A pharmaceutical composition comprising the compound of claim 8 and a pharmaceutically acceptable vehicle.

19. The compound having the structure:
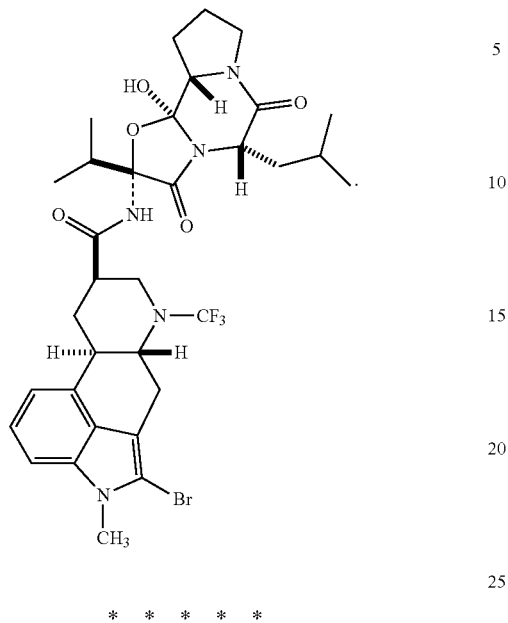

UNITED STATES PATENT AND TRADEMARK OFFICE
CERTIFICATE OF CORRECTION

PATENT NO. : 8,710,092 B2
APPLICATION NO. : 12/978314
DATED : April 29, 2014
INVENTOR(S) : Zhang et al.

It is certified that error appears in the above-identified patent and that said Letters Patent is hereby corrected as shown below:

On the Title Page, Item (57), under "Abstract", in column 2, line 9, delete "and or" and insert -- and/or --, therefor.

In the Specification

In column 1, line 17, delete "and or" and insert -- and/or --, therefor.

In column 11, lines 17-18, after "esters" delete "enol ethers,".

In column 11, line 25, delete "parsomnia and hyperlactinemia" and insert -- parasomnia and hyperprolactinemia --, therefor.

In column 12, line 67, delete "propenyls" and insert -- propanyls --, therefor.

In column 14, line 63, delete "—O—O," and insert -- —O—O—, --, therefor.

In column 14, line 64, delete "O—S—," and insert -- —O—S—, --, therefor.

In column 15, line 34, delete "heteroarylakenyl" and insert -- heteroarylalkenyl --, therefor.

In column 15, line 44, delete "it" and insert -- π --, therefor.

In column 17, line 34, delete "—S(O)$_{20}$," and insert -- —S(O)$_2$O$^-$, --, therefor.

In column 17, line 35, delete "—S(O)$_2$OR$^b$," and insert -- —OS(O)$_2$OR$^b$, --, therefor.

In column 17, line 36, delete "(O)," and insert -- (O$^-$), --, therefor.

In column 17, line 49, delete "—O(O)$_2$OR$^b$," and insert -- —OS(O)$_2$OR$^b$, --, therefor.

In column 17, line 51, delete "C(O)NR$^c$R$^c$," and insert -- —C(O)NR$^c$R$^c$, --, therefor.

In column 17, line 65, delete "mammal" and insert -- mammal. --, therefor.

In column 26, line 62, delete "R$_{1015}$," and insert -- R$_{105}$, --, therefor.

In column 39, line 7, delete "homallyl" and insert -- homoallyl --, therefor.

In column 41, line 46, after "determined" insert -- . --.

In column 43, line 28, delete "crosscarmellose" and insert -- croscarmellose --, therefor.

Signed and Sealed this
Seventh Day of October, 2014

Michelle K. Lee
*Deputy Director of the United States Patent and Trademark Office*

CERTIFICATE OF CORRECTION (continued)

U.S. Pat. No. 8,710,092 B2

In column 43, line 43, delete "laural" and insert -- lauryl --, therefor.

In column 46, lines 39-40, delete "carboxymethylcelluose" and insert -- carboxymethylcellulose --, therefor.

In column 48, line 41, delete "sorbital," and insert -- sorbitol, --, therefor.

In column 49, line 35, delete "iotophoretic" and insert -- iontophoretic --, therefor.

In column 49, line 66, delete "U U.S." and insert -- U.S. --, therefor.

In column 51, lines 43-44, delete "parsomnia and hyperlactinemia" and insert -- parasomnia and hyperprolactinemia --, therefor.

In column 55, line 39, delete "parsomnia and hyperlactinemia" and insert -- parasomnia and hyperprolactinemia --, therefor.

In column 56, line 62, delete "parsomnia and hyperlactinemia" and insert -- parasomnia and hyperprolactinemia --, therefor.

In column 57, line 12, delete "parsomnia and hyperlactinemia" and insert -- parasomnia and hyperprolactinemia --, therefor.

In column 57, line 23, delete "and or" and insert -- and/or --, therefor.